(12) United States Patent
Nakamura et al.

(10) Patent No.: US 8,196,230 B2
(45) Date of Patent: Jun. 12, 2012

(54) AUTOMATIC TREATING DEVICE FOR URINATION AND DEFECATION

(75) Inventors: Minoru Nakamura, Hiroshima (JP); Kim Yong Ha, Yongin-si (KR); Do Hyun Ok, Suwon-si (KR)

(73) Assignees: Minoru Nakamura, Hiroshima-shi (JP); Sanyo Tech Co., Ltd., Gyeonggi-do (KR)

( * ) Notice: Subject to any disclaimer, the term of this patent is extended or adjusted under 35 U.S.C. 154(b) by 855 days.

(21) Appl. No.: 12/289,084

(22) Filed: Oct. 20, 2008

(65) Prior Publication Data

US 2009/0193571 A1 Aug. 6, 2009

(30) Foreign Application Priority Data

Feb. 5, 2008 (JP) ................................. 2008-025772

(51) Int. Cl.
*E03D 1/00* (2006.01)
(52) U.S. Cl. ..................................... 4/321; 4/455; 4/456
(58) Field of Classification Search ............. 4/447, 450, 4/454–456, 144.1, 144.3, 319, 320; 604/327, 604/346, 347, 348, 351, 353; 5/695
See application file for complete search history.

(56) References Cited

U.S. PATENT DOCUMENTS

| 2,886,827 A | * | 5/1959 | Washington ....................... 4/456 |
| 4,791,686 A | | 12/1988 | Taniguchi et al. |
| 5,681,297 A | | 10/1997 | Hashimoto et al. |
| 6,848,133 B2 | * | 2/2005 | Tanaka ............................... 5/604 |
| 2002/0010446 A1 | | 1/2002 | Maimets |

FOREIGN PATENT DOCUMENTS

| EP | 0 200 174 A2 | 11/1986 |
| JP | B-13-12129 | 8/1938 |
| JP | B-50-27822 | 8/1975 |
| JP | A-51-93588 | 8/1976 |

(Continued)

OTHER PUBLICATIONS

Jan. 5, 2010 Office Action issued in Japanese Patent Application No. 2008-025772 (with translation).

*Primary Examiner* — Gregory Huson
*Assistant Examiner* — Janie Christiansen
(74) *Attorney, Agent, or Firm* — Oliff & Berridge, PLC

(57) ABSTRACT

A toilet unit for use in a supine position comprises a depressed section formed on a mattress, a U-shaped casing adapted to mount a butt-pad provided with a U-shaped central groove section thereon, and a urination and defecation treating unit of a substantially T-shape loosely fitted into the U-shaped central groove section of the butt-pad. The urination and defecation treating unit comprises a lateral casing of which the inside is formed in a boat shape to discharge urination and defecation externally by water discharged from a nozzle provided on the bottom section and a vertical casing having a nozzle provided in front for washing the buttocks and private parts of a human body and then drying the buttocks and private parts by an air supply, wherein a dead end of the lateral casing of the urination and defecation treating unit is communicatively connected to a storage tank through a discharge pipe, and various nozzles provided on the lateral and vertical casings are communicatively connected to a wash water supply section through a nozzle operating section designed to control the water and air supply.

1 Claim, 24 Drawing Sheets

FOREIGN PATENT DOCUMENTS

| | | |
|---|---|---|
| JP | U-60-94223 | 6/1985 |
| JP | U-61-16125 | 1/1986 |
| JP | U-64-3624 | 1/1989 |
| JP | A-08-322868 | 10/1996 |
| JP | A-11-290396 | 10/1999 |
| JP | A-2003-144497 | 5/2003 |
| JP | A-2008-11999 | 1/2008 |
| JP | A-2008-029758 | 2/2008 |
| WO | WO 2006/046532 A1 | 5/2006 |

* cited by examiner

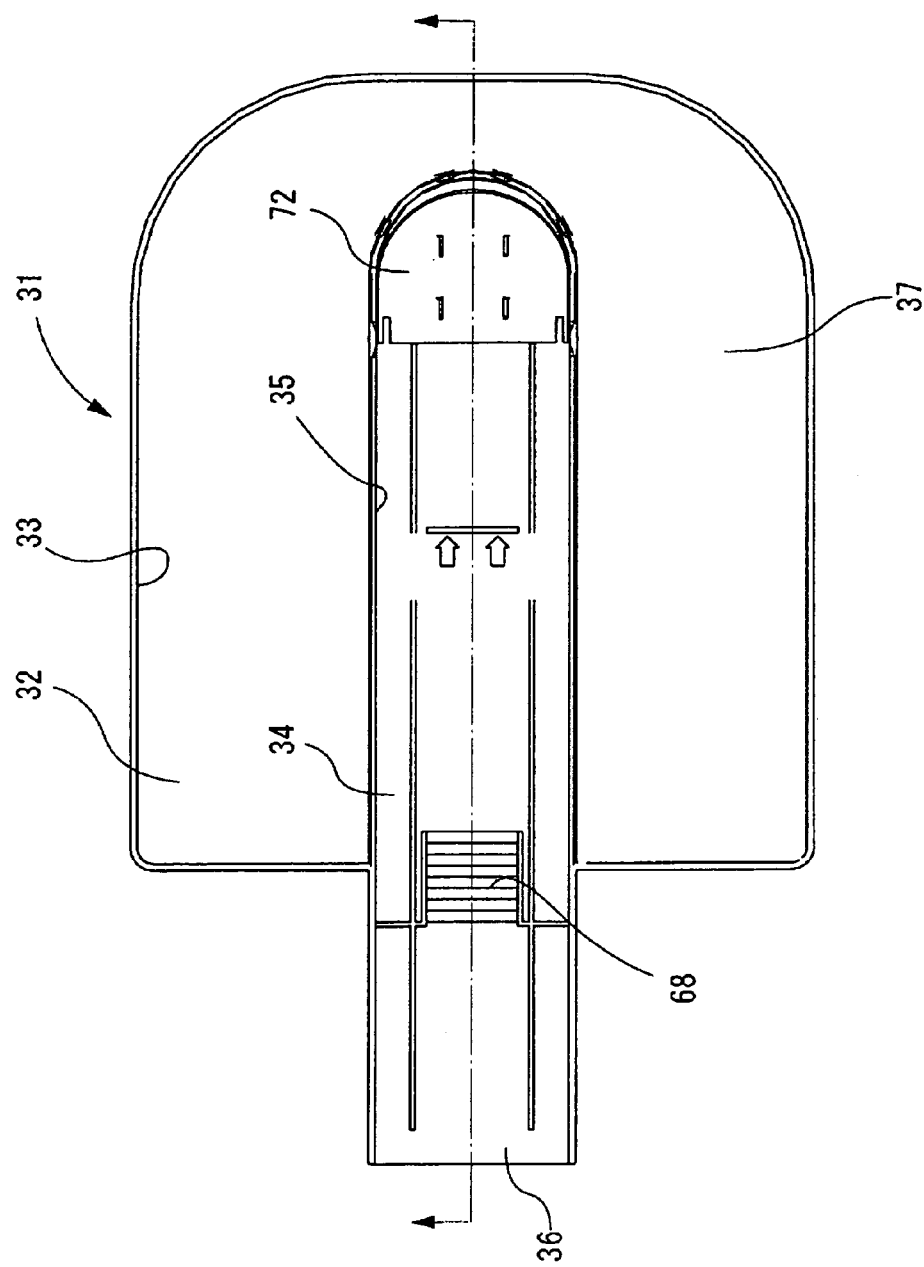

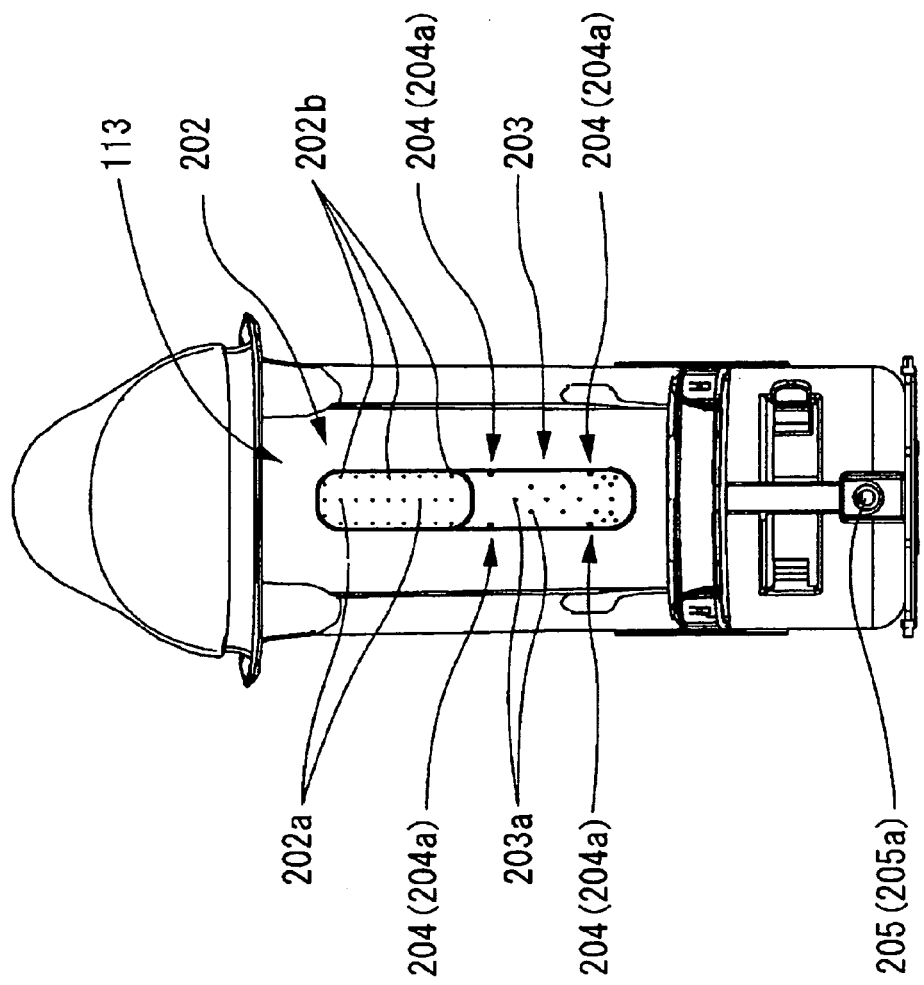

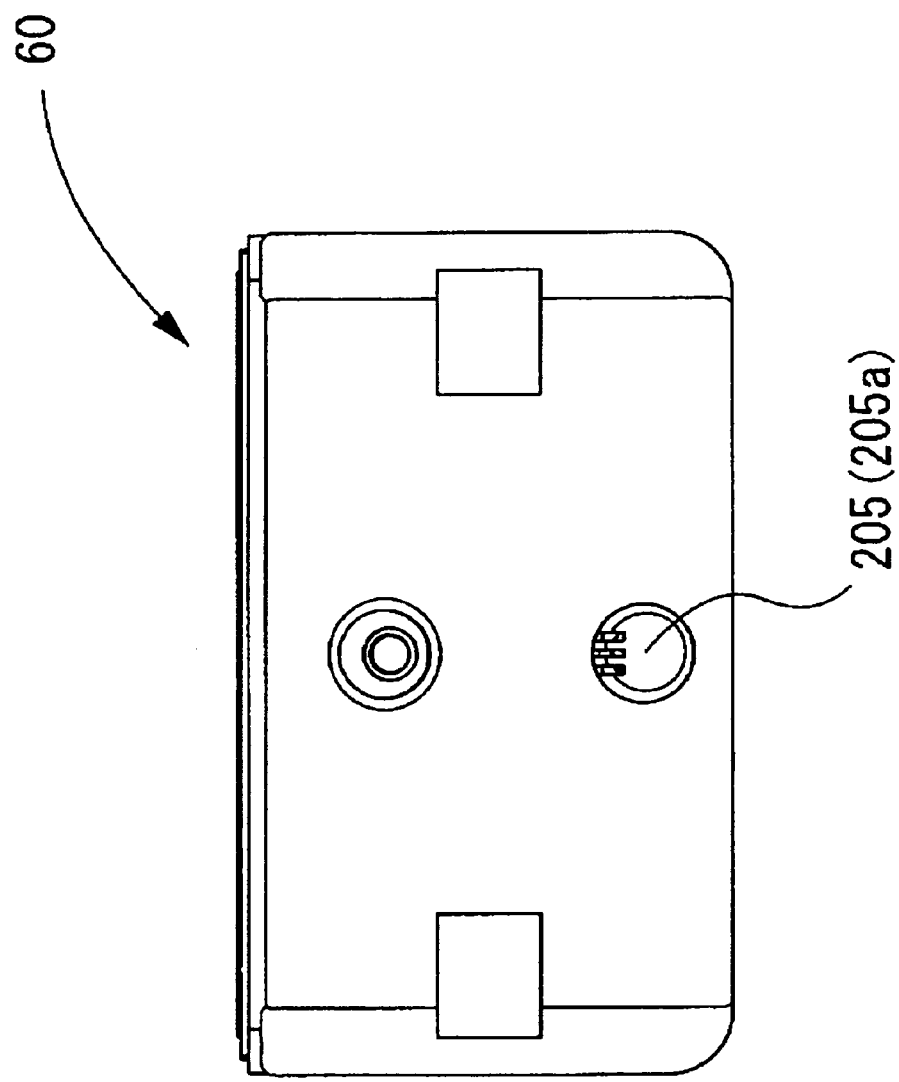

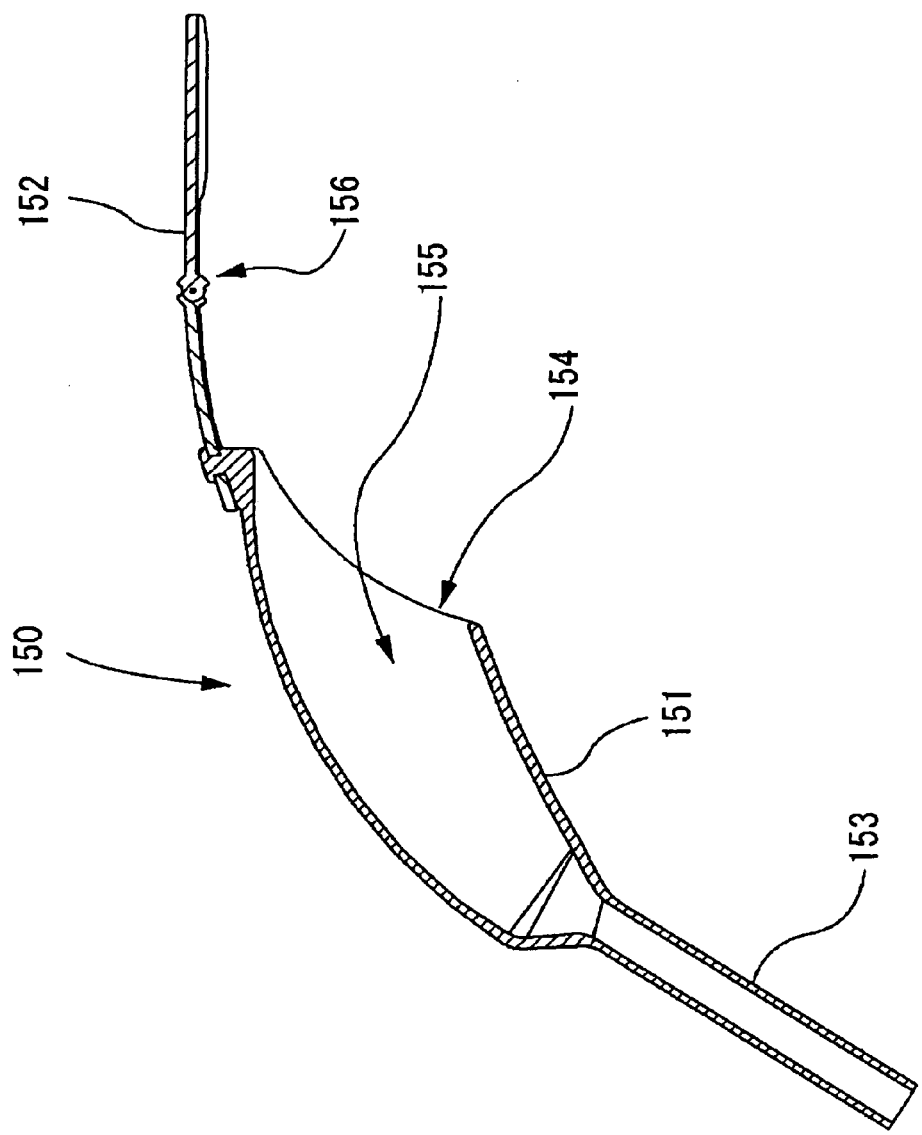

AUTOMATIC TREATING DEVICE FOR URINATION AND DEFECATION

BACKGROUND OF THE INVENTION

1. Field of the Invention

The present invention relates to an automatic treating device for urination and defecation whereby a bed-ridden patient and/or an aged person can treat his urination and defecation in a supine position without someone else's assistance.

2. Description of the Prior Art

Various diapers and equipment have been devised in the prior art whereby bed-ridden patients and/or aged people can urinate and defecate and treat the urination and defecation in a supine position without any assistance from others. For examples, Patent Document 1 discloses a technique in which a urination and defecation treating body of a substantially L-shape as seen from the side is provided with a stool detection sensor and various nozzles.

Referring to this technique, when the patient urinates and defecates, he mounts his haunch on the urination and defecation treating body while holding tight an upright section of the urination and defecation treating body in the crotch of his legs. After defecation, the stool detection sensor consisting of a proximity sensor detects the stools to automatically cause wash water to spout through various nozzles, thereby washing not only the private parts of the patient, but also the inside of the urination and defecation treating body. The stools are then discharged to the outside from a waste suction hose. In this manner, the defecation treatment of the bed-ridden patients can be performed automatically.

Patent Document 2 discloses an automatic defecation treating device comprising a diaper-shaped casing of a substantially L-shape with a box type structure which is long in the longitudinal direction, a plurality of sensors for detecting excretory substances, a plurality of nozzles for injecting wash water to the excretory substances to perform predetermined washing, and a diaper frame in which various nozzles are installed. The plurality of nozzles consecutively provided on the diaper-shaped casing comprises an anal nozzle for washing the anal area, a bidet nozzle for washing the private parts, a buttocks nozzle for washing the buttocks area, and a stool nozzle for crushing urination and defecation materials and discharging these to the outside. Each nozzle is also provided with a function for drying the buttocks and private parts. Each sensor comprises a stool detection sensor for detecting the discharged stools and a urine detection sensor for detecting the discharged urine.

Patent Document 1: Japanese Unexamined Patent Publication No. Hei 8-322868

Patent Document 2: Japanese Patent Application No. 2006-209168

However, the automatic defecation treating device described above has the following problems. First, in such an automatic defecation treating device, the diaper-shaped casing is directly mounted on a bed. Accordingly, once a leak of wash water and urine and stools is caused between the bed and the diaper-shaped casing, there is a worry that the leakage will spread over the reverse side of the bed and wet it. Second, it is very troublesome for the patient to fit the diaper-shaped casing into the crotch of his legs. Third, it is not enough to fit the diaper-shaped casing in the crotch of the patient's legs. Fourth, when the diaper-shaped casing is fitted in the crotch of the legs of the patient who is in a supine position, the buttocks outside the diaper-shaped casing are not sufficiently stabilized and pain is caused to the buttocks and the crotch of the legs of the patient. Fifth, a frame formed for the diaper is separately provided and this makes a structure of the diaper-shaped casing complicated.

SUMMARY OF THE INVENTION

It is therefore an object of the present invention to provide an automatic treating device for urination and defecation having a toilet unit for use in a supine position which is resistant to leakage, can be readily installed, can improve the fit when installed, can be used without pain, and can simplify the entire structure.

BRIEF DESCRIPTION OF THE DRAWINGS

The above and other objects, features and advantages of the present invention will become more apparent from the following description when taken in conjunction with the accompanying drawings.

FIG. 5A is a front view of a U-shaped casing and FIG. 5B is a cross-sectional view of the U-shaped casing;

FIG. 12 is a front view of various nozzles;

FIG. 13C is a rear view thereof, FIG. 14A is a perspective view of a urine collecting device and FIG. 14B is a cross-sectional view of the same;

DETAILED DESCRIPTION OF THE PREFERRED EMBODIMENTS

Preferred embodiments of the present invention will now be described with reference to the accompanying drawings.

Figure 1:
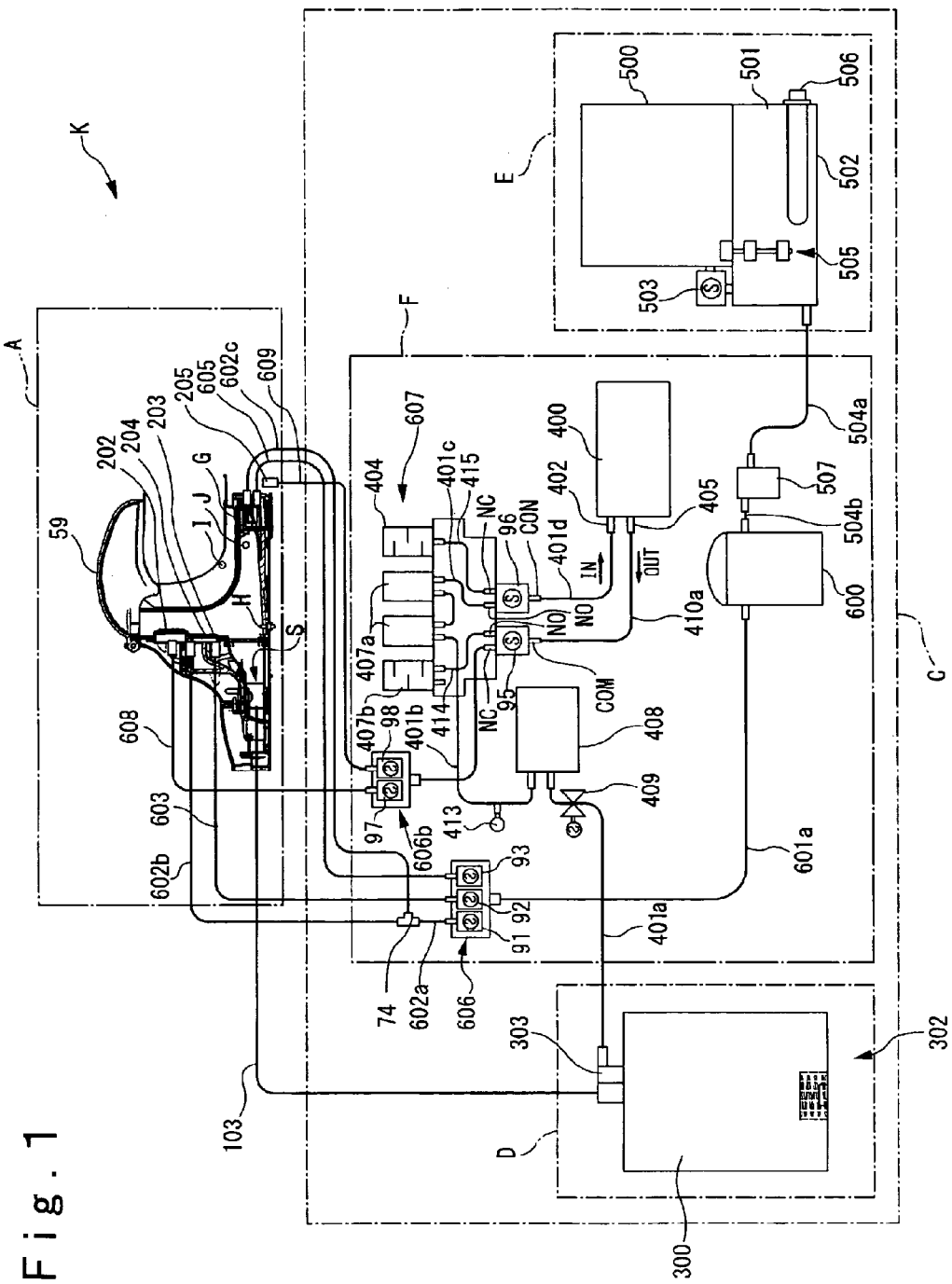
FIG. 1 is a view showing the structure of an automatic treating device for urination and defecation according to an embodiment of the present invention.

As shown in FIG. 1, reference alphabet A shows a toilet unit for use in a supine position. A patient urinates and defecates holding the toilet unit A according to the present invention in the crotch of his legs in a supine position. Urine and stools are then automatically sent to a storage tank from the toilet unit A. The toilet unit A is designed to wash the buttocks, private parts and the like of the patient and then dry these using an air supply.

Figure 2:
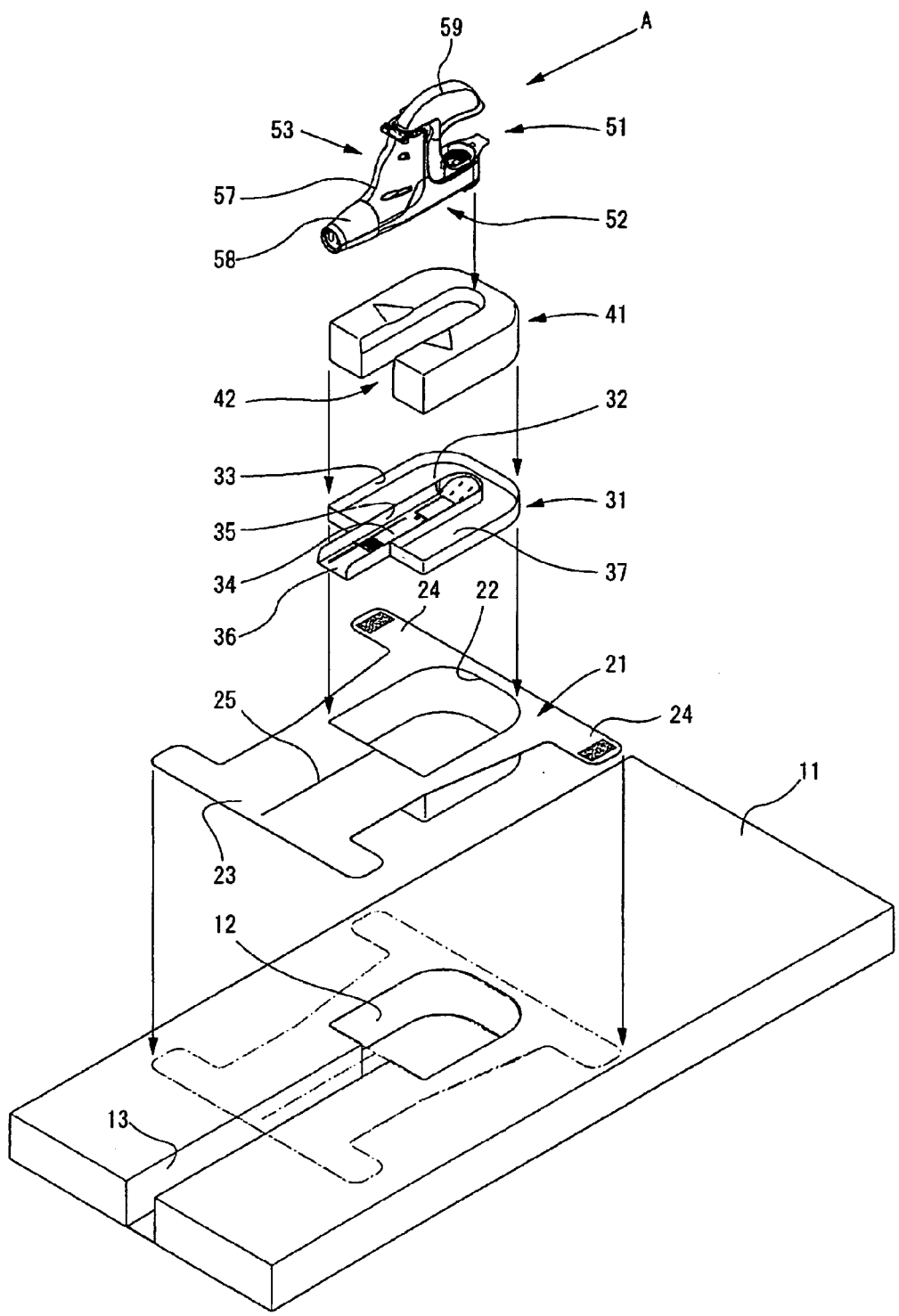
FIG. 2 is a perspective view of the external appearance of the automatic treating device for urination and defecation.

As shown in FIG. 2, the toilet unit A is provided in such a manner that a depressed section 12 is formed in the middle of a mattress 11, made of urethane, which has such an area that the patient can lie supine. One side of the depressed section 12 communicates with a pipe passage 13 formed on the mattress 11.

Figure 4:
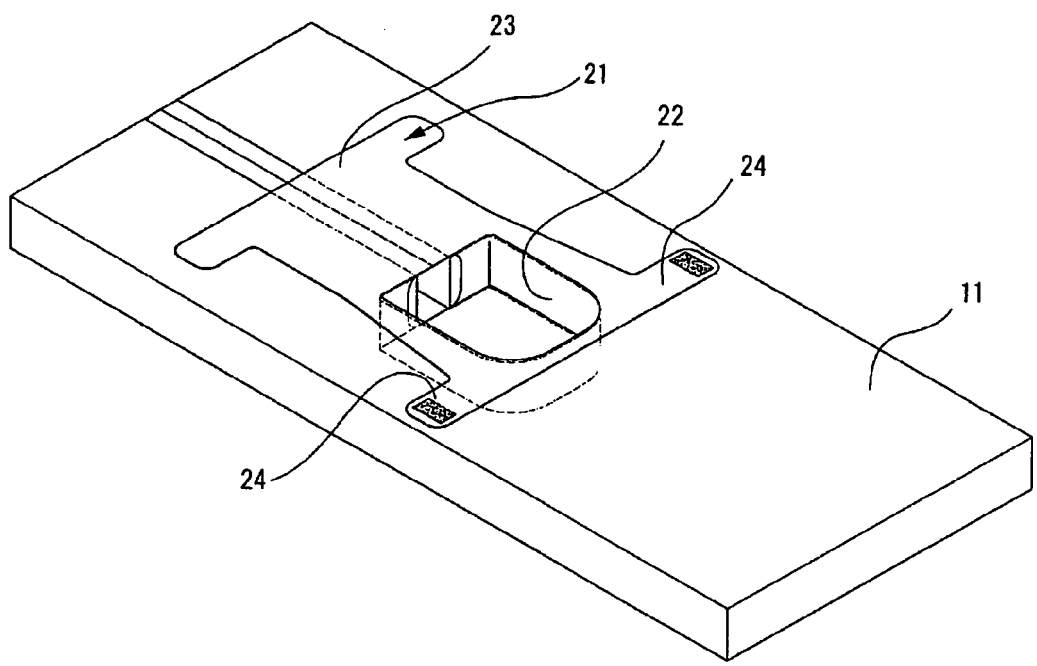
FIG. 4 is a perspective view showing a condition in which a diaper has been fitted on the mattress.

As shown in FIGS. 2 and 4, the depressed section 12 is formed in a substantially rectangular shape. A diaper 21 made of paper or cloth, which has an opening 22, in the center, corresponding to the depressed section 12 is put on the depressed section 12. The diaper 21 is provided in such a manner that a crotch covering section 23 extended on the downstream side of the diaper 21 and a turnover section 24 extended, in the lateral direction, on the upstream side protrude from the outer periphery of the depressed section 12 while causing the opening 22 to correspond to the depressed section 12.

A U-shaped casing 31 of a substantially rectangular shape described later is fitted into the depressed section 12. A substantially U-shaped butt-pad 41 made of urethane is mounted on the U-shaped casing 31. A lateral casing 52 of a substantially L-shape of the urination and defecation treating unit 51 is loosely fitted into a U-shaped central groove section 42 of the butt-pad 41 so that a vertical casing 53 of a substantially L-shape of the urination and defecation treating unit 51 protrudes upwards from the upper surface of the butt-pad 41.

Figure 9:
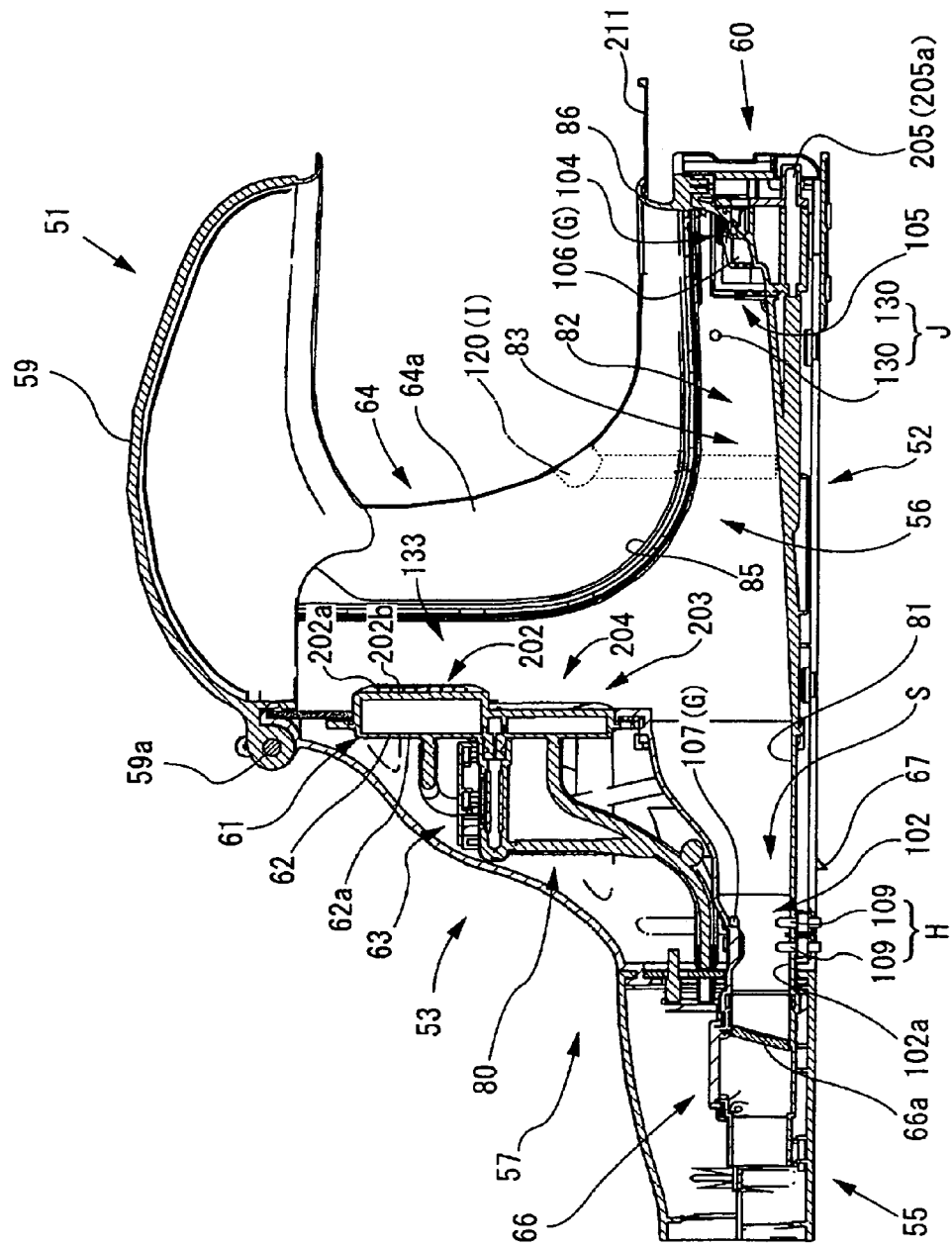
FIG. 9 is a cross-sectional view of the urination and defecation treating unit.

The patient lies supine on the mattress 11 and mounts his buttocks on the butt-pad 41. As shown in FIG. 9, the patient urinates and defecates on the boat-shaped inside of the lateral casing 52 of a substantially L-shape holding the vertical casing 53 of a substantially L-shape of the urination and defecation treating unit 51 in the forks of his legs, wherein urine and stools are then discharged out of the urination and defecation treating unit 51 by the water discharged from an injection nozzle 105 provided on the head of the lateral casing 52. The buttocks and private parts of the patient are then washed by the wash water emitted from a washing nozzle 203 and a bidet nozzle 202 provided on the vertical casing 53 of the urination and defecation treating unit 51. The buttocks are also washed by the wash water discharged from a buttocks-nozzle 104 provided on the lateral casing 52 of the urination and defecation treating unit 51. Then, the buttocks and private parts of the patient are dried by the air blasting from a drying nozzle 204 and an air supply nozzle 205.

(i) The diaper 21 to be spread on the periphery of the depressed section 12 will now be described.

As shown in FIGS. 2 and 4, the diaper 21 is provided in the center with the opening 22 corresponding to the depressed section 12. Extended on the downstream side of the opening 22 is the crotch covering section 23 for covering the crotch of the patient's legs, while extended on the upstream side of the opening 22 is the laterally projecting turnover section 24.

The diaper 21 is mounted on the mattress 11 in a spread-out manner to surround the periphery of the depressed section 12. The center of the crotch covering section 23 of the diaper 21 is provided with a cutting-plane line 25 to be joined or separated by a zipper. Another end of the zipper is ended in the middle of the crotch covering section 23. Thus, the crotch covering section 23 expands laterally from the cutting-plane line 25 and the urination and defecation treating unit 51 described later can readily pass through, when fitted, the U-shaped groove section 42 of the substantially U-shaped butt-pad 41 described later, which is fitted into the depressed section 12 of the mattress 11, without causing interference with the diaper 21.

Steps for putting the diaper 21 on the patient will now be described.

Figure 3:
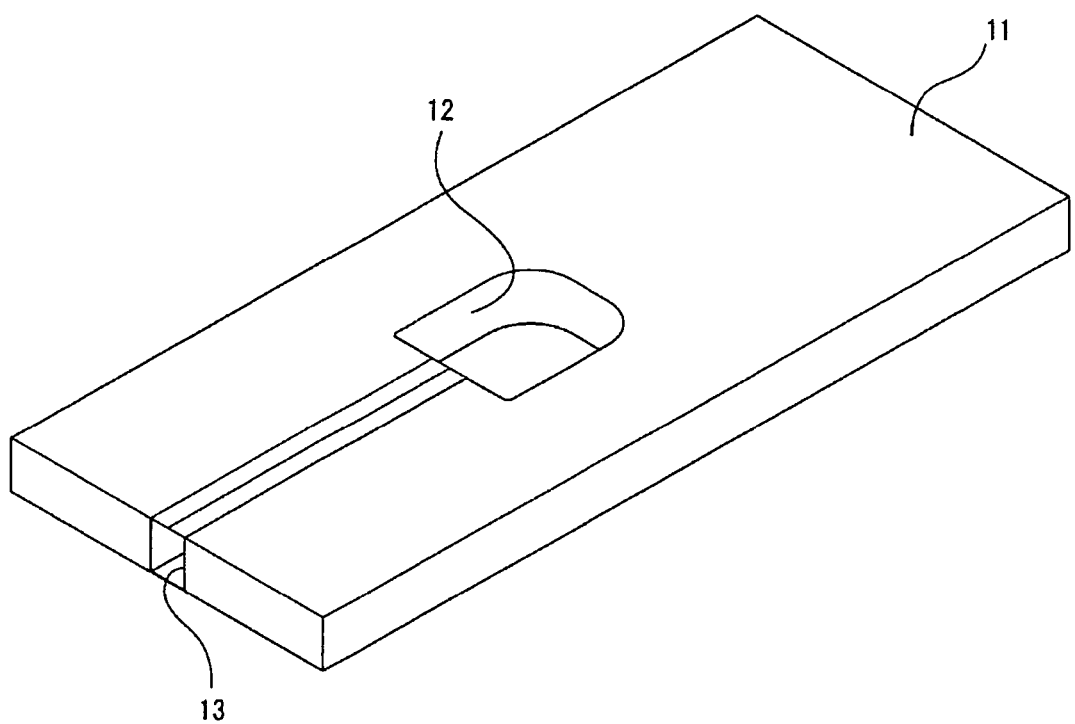
FIG. 3 is a perspective view of a mattress.

As shown in FIGS. 2 through 4, the diaper 21 provided in the center with the opening 22 corresponding to the depressed section 12 of the mattress 11 is put on the depressed section 12 to cause the opening 22 to correspond to the depressed section 12, wherein the crotch covering section 23 extended on the downstream side of the diaper 21 and the turnover section 24 extended on the upstream side thereof protrude to the outer periphery of the depressed section 12.

Now, the U-shaped casing 31 is fitted into the opening 22 of the diaper 21 and the butt-pad 41 is mounted on the U-shaped casing 31, wherein a care provider causes the patient's buttocks to mount on the butt-pad 41 to bring the supine patient in a supine position on the mattress 11.

Next, the diaper 21 is caused to expand laterally from the cutting-plane line to produce an opening. The toilet unit A for use in a supine position to which a discharge pipe 103 is connected is inserted into the laterally expanded opening to be fitted into the U-shaped groove section 42 of the butt-pad 41. The toilet unit A is then held in the crotch of the legs of the patient, wherein the private parts of the patient are hidden from view by a cover body 59. In this case, the crotch of the patient's legs is brought into a close contact with electrode terminals 120, 120 of a fitting sensor I at a constant pressure.

Then, the right and left ends of the turnover section 24 of the diaper 21 are wrapped around an abdominal part of the patient to fold and each tape of the turnover section 24 is fastened. After covering the cover body 59 with the crotch covering section 23 of the diaper 21, each tape provided at the dead end section of the crotch covering section 23 is fastened to the turnover section 24 of the abdominal part to complete an fitting operation of the toilet unit A for use in a supine position.

(ii) The U-shaped casing 31 will now be described.

Figure 5B:
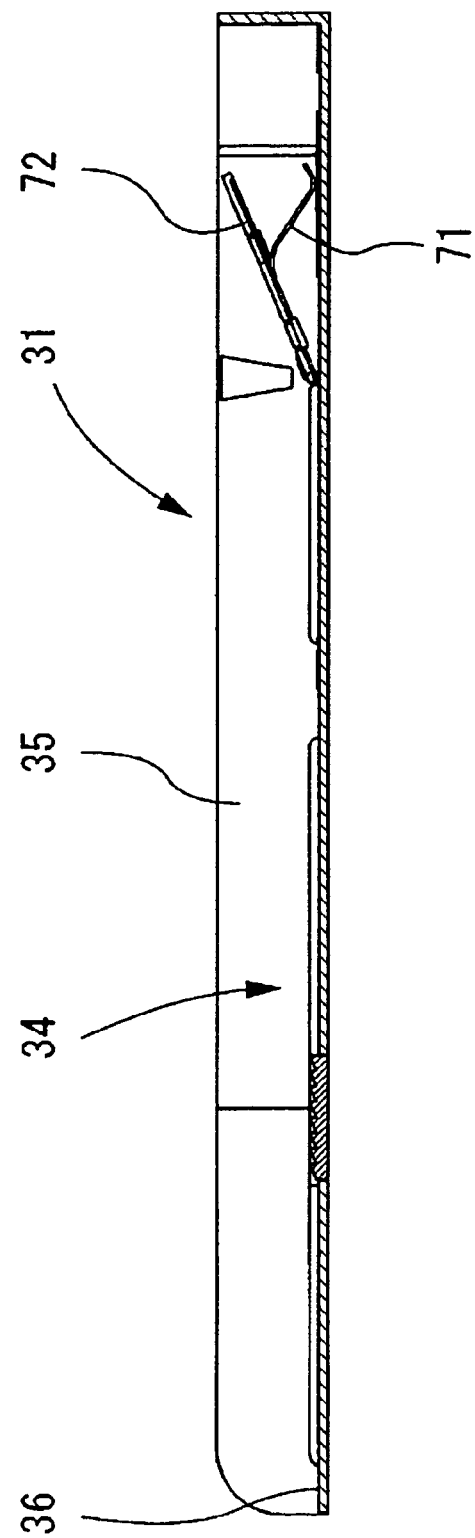

As shown in FIGS. 2 and 5, the U-shaped casing 31 has a shape corresponding to a substantially rectangular shape of the depressed section 12 and a guide wall stands upright on the peripheral edge. In other words, the U-shaped casing has an outer shape which can be loosely fitted into the depressed section 12. An outer peripheral wall 33 stands upright at the outer peripheral edge of a bottom plate 32 at least in a condition lower than the thickness of the butt-pad 41 described later. Further, longitudinally provided in the center of the bottom plate 32 is a band-shaped central guide passage 34. Both sides of the guide passage 34 are provided with a guide wall 35.

The guide passage 34 protrudes outside the outer peripheral wall 33 on the downstream side. Accordingly, when the U-shaped casing 31 is fitted into the depressed section 12 of the mattress 11, a protruding section 36 of the guide passage 34 is caused to be inserted in a pipe passage 13 which communicates with the depressed section 12.

The butt-pad 41 of a substantially U-shape described later is fitted and held in a U-shaped space 37 provided in the center of the U-shaped casing 31 constituted above.

(iii) The butt-pad 41 will now be described.

Figure 6:
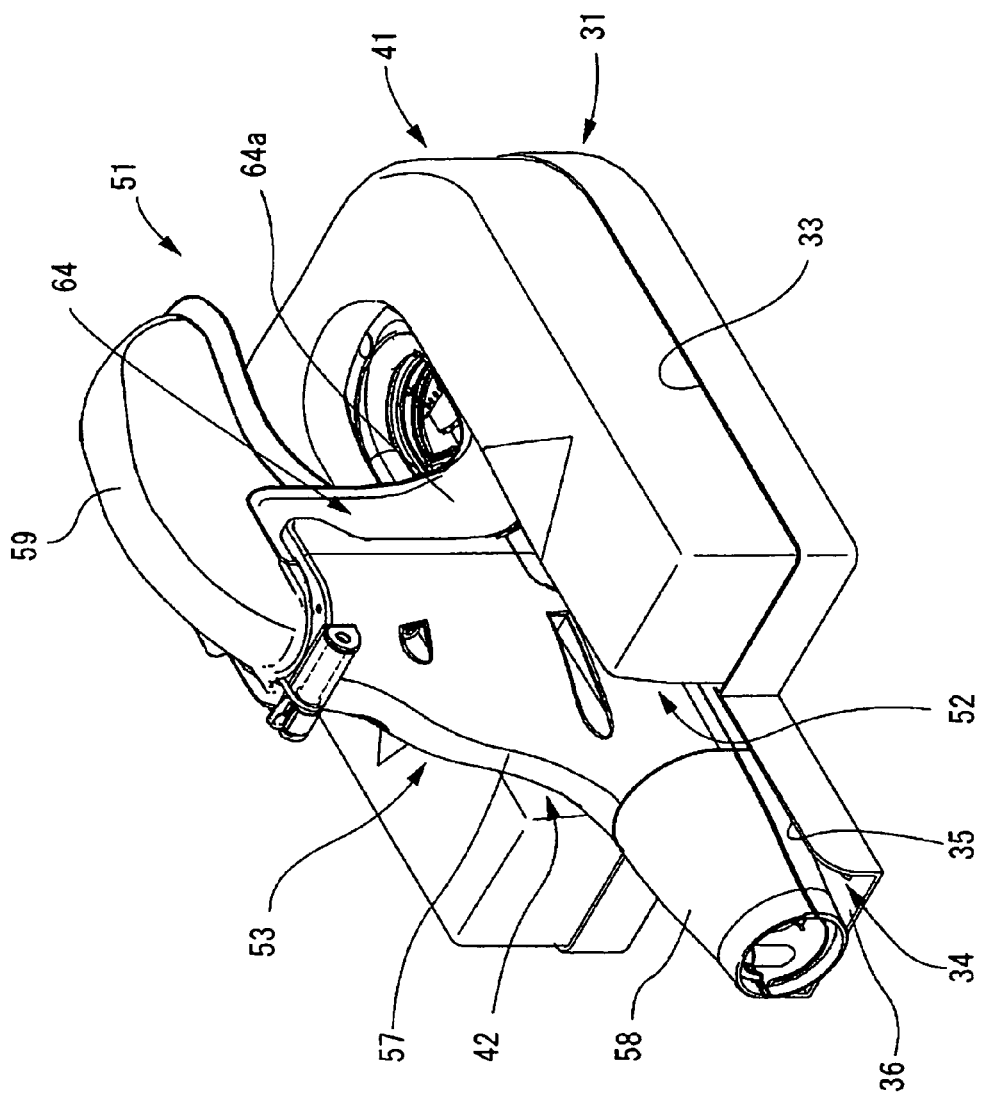
FIG. 6 is a schematic view showing a condition in which a urination and defecation treating unit has been fitted into the U-shaped case.
Figure 7:
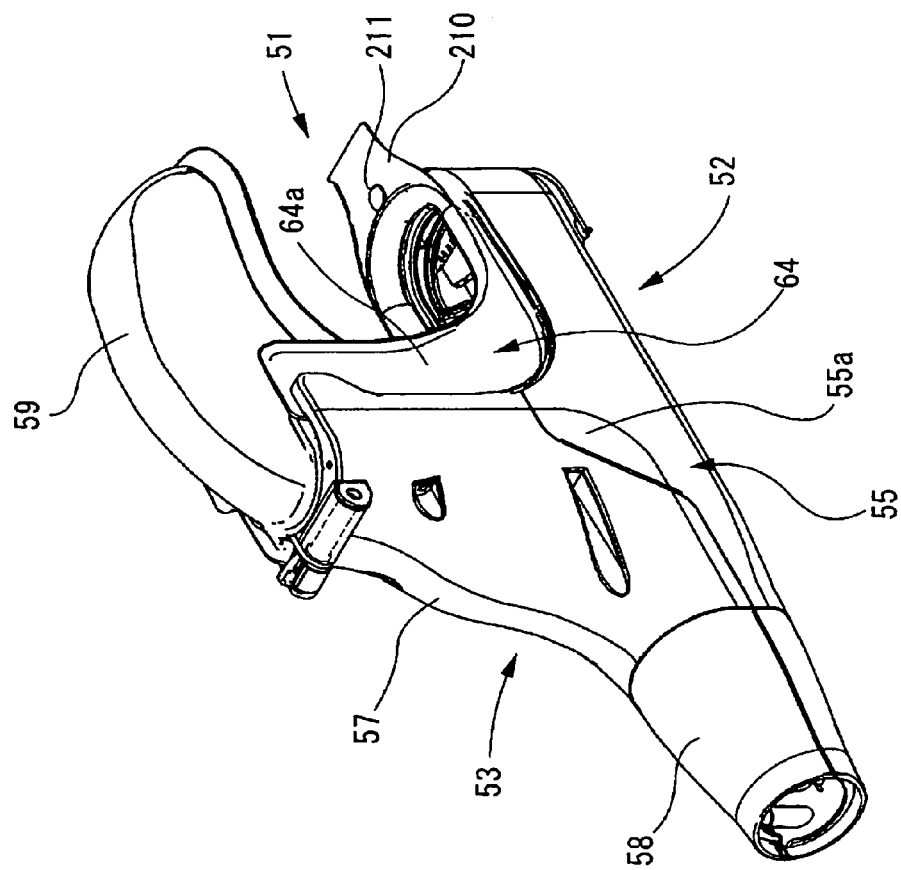
FIG. 7 is a perspective view of the urination and defecation treating unit.

As shown in FIGS. 2 and 6, the butt-pad 41 is provided in such a manner that the guide wall 35 of the guide passage 34 of the U-shaped casing 31 can be fitted into the U-shaped central groove section 42.

The butt-pad 41 uses raw material in which flexible material such as urethane is included. In particular, it is necessary for the material to excel not only in water-proofing, waterrepellent and water-absorbing properties, but also in a ventilation property which does not hold humidity. It is also necessary to provide material and feel which can prevent bedsores in the patient.

The thickness of the butt-pad 41 is at least equivalent to that of the depressed section 12 of the mattress 11 and is set higher than the outer peripheral wall 33 of the U-shape casing 31.

In the condition in which the butt-pad 41 is fitted into the U-shaped space 37 of the U-shaped casing 31, the central groove section 42 of the butt-pad 41 is integral with the guide passage 34.

Further, the U-shaped space 37 described later of the U-shaped casing 31 is effective in storing water leakage and preventing the water leakage from wetting the reverse side of the mattress 11 even though the wash water leaking from the inside of the urination and defecation treating unit 51 infiltrates from the peripheral surface of the butt-pad 41.

(iv) The urination and defecation treating unit 51 will be described below.

Figure 8:
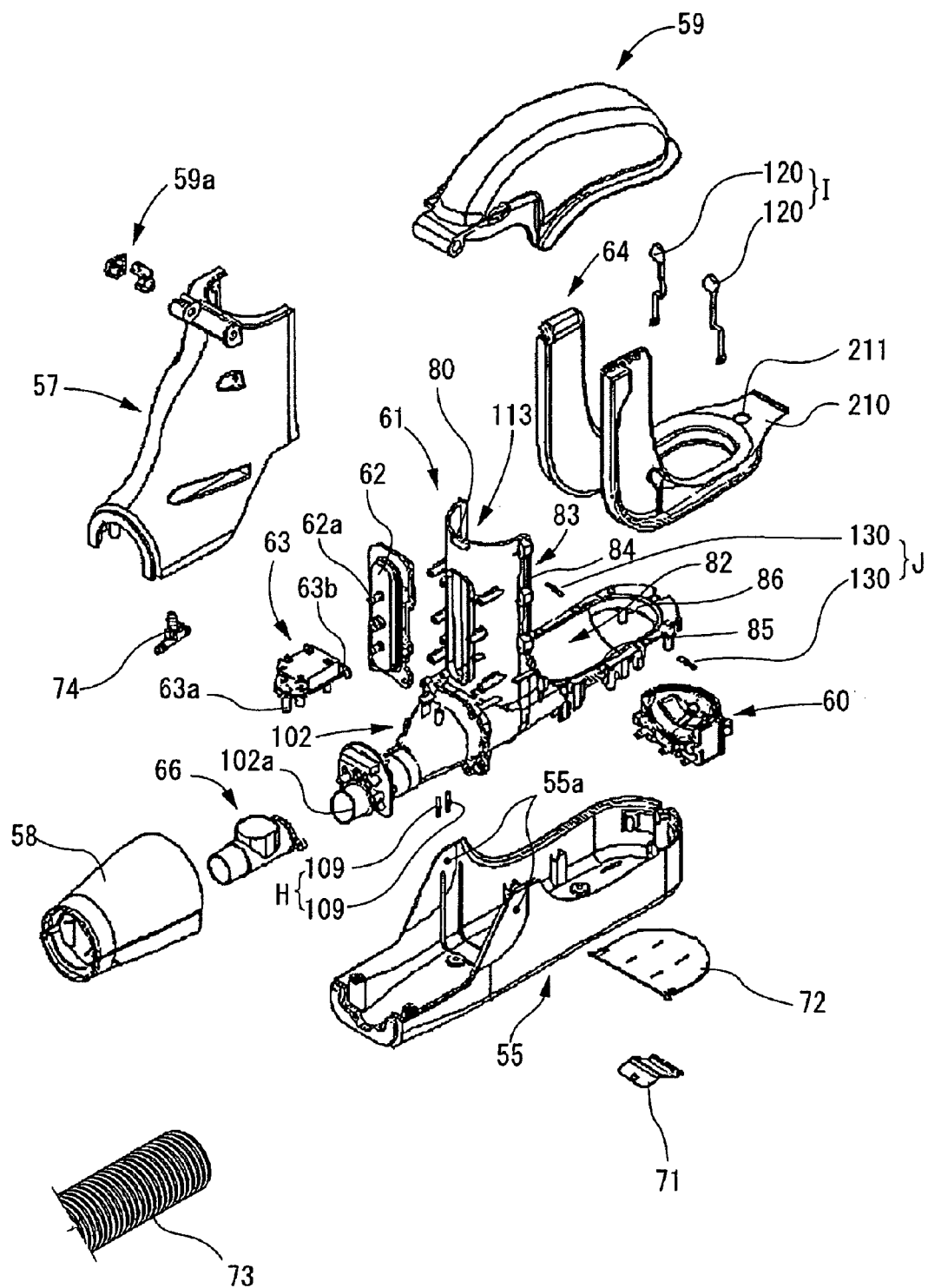
FIG. 8 is an exploded perspective view of the urination and defecation treating unit.

As shown in FIGS. 2 and 8, the urination and defecation treating unit 51 comprises a support casing 55 of a substantially oblong shape which is fitted into the guide passage 34 of the U-shaped casing 31, in other words, the U-shaped central groove section 42 of the butt-pad 41, and treating body 56 of a substantially T-shape which is fitted into and housed in the support casing 55. The treating body 56 is designed to have a predetermined rigidity so that the urination and defecation treating unit 51 is not distorted by the patient's weight.

As shown in FIGS. 8 and 9, the support casing 55 is provided with a peripheral wall on the periphery to form a boat shape in which the treating body 56 (described later) is housed. The right and left side walls of the support casing 55 are upraised in a chevron shape in the center. These upraised sections 55a and an opening edge of the latter half section of the support casing 55 are provided to allow a vertical member 57 to be fitted therein. The vertical member 57 is formed in a semicircular arc shape in cross-section and in a substantially L-shape as seen from the side to cover the backside of a vertical member of the treating body of a substantially T-shape 56 described later and part of the upper surface of the treating body 56.

Connected to an end opening on the downstream side formed by assembly of the support casing 55 and the vertical member 57 is a cylindrical casing 58 into which a discharge passage 81 for urine and stools provided at the downstream end of the treating body 56 described later and a discharge pipe 103 (refer to FIG. 1) in communication with the discharge passage 81 are inserted.

Further, a cover body 59 adapted to cover the private parts of the patient from view is pivotally attached to the upper edge of the vertical member 57 which covers the backside of a vertical casing 80 of the treating body 56.

The cover 59 is formed in a dome shape and the rear anchor is pivotally attached to the upper end of the vertical member 57, which is formed in a semicircular arc shape in cross section, through a pin 59a. The cover body 59 is provided to openably and closably cover the private parts of the patient from view in a condition in which the patient holds the treating body 56 in the crotch of his legs.

In this manner, the treating body 56 can be fully covered by the support casing 55, the vertical member 57, the cylindrical casing 58 and the cover body 59, except for a projected nozzle section adapted to carry out a necessary urination and defecation treating function.

Such a treating body 56 is formed in a substantially U-shape by a urination and defecation container 82 serving as a lateral casing of which the inside is formed in a boat shape and a washing nozzle retainer 61 serving as a vertical casing which stands upright at the downstream end of the urination and defecation container 82.

Figure 13A:
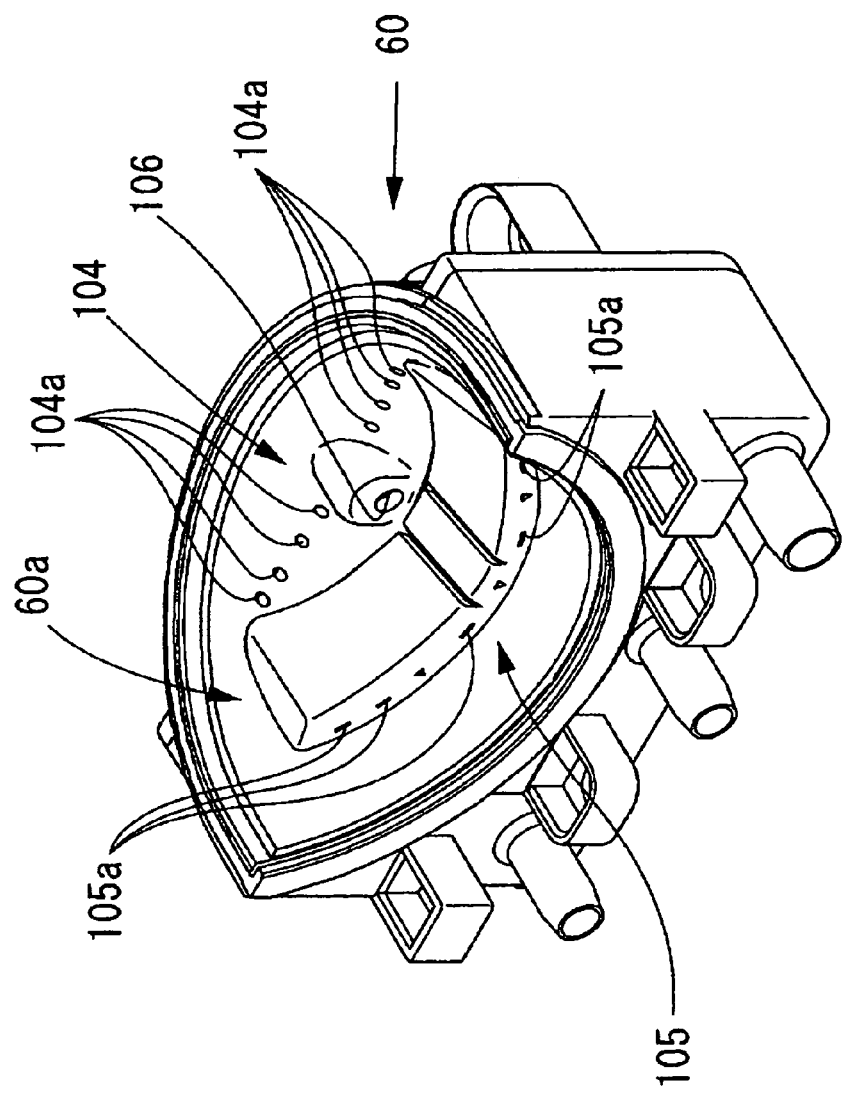
FIG. 13A is a perspective view of a front end nozzle bracket.
Figure 13B:
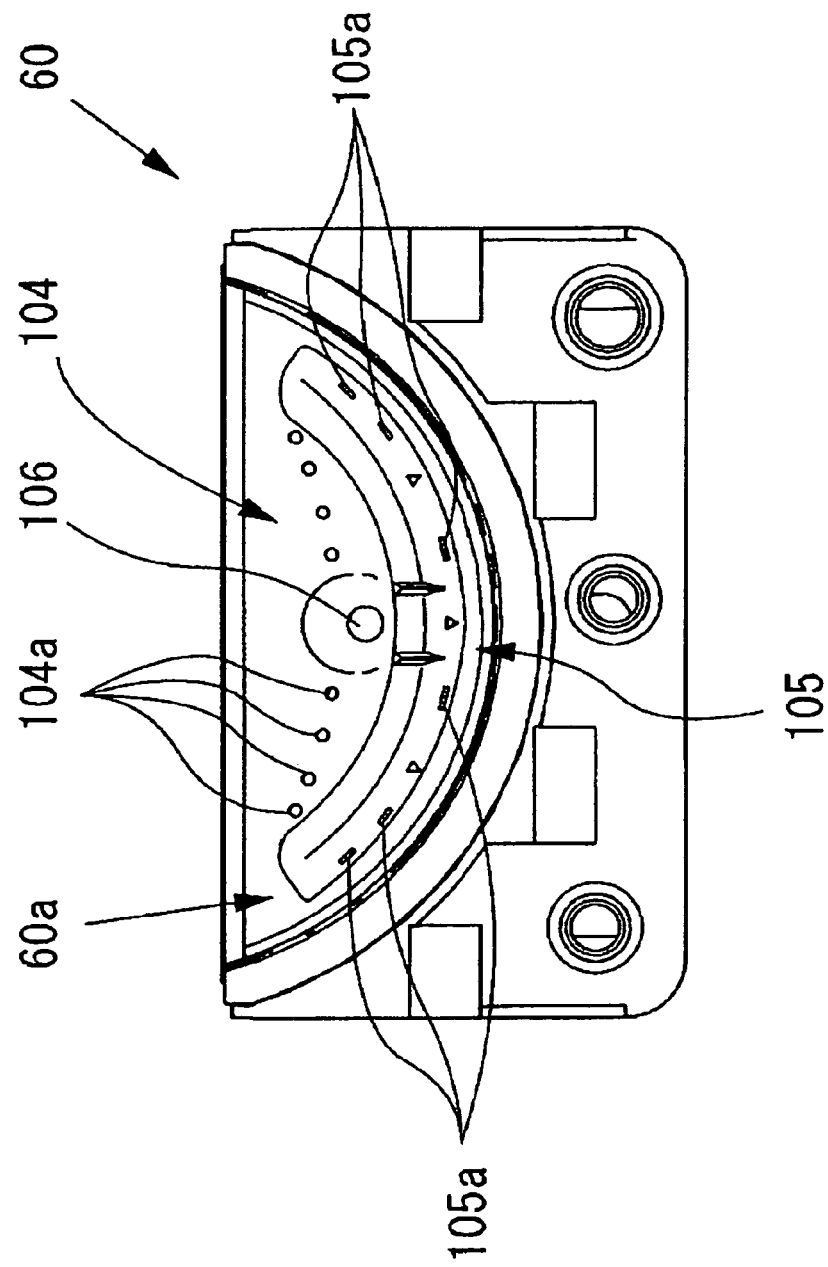
FIG. 13B is a front view the front end nozzle bracket.

As shown in FIGS. 8 and 13, a front end nozzle bracket 60 is provided at the front end of the urination and defecation container 82. The front end nozzle bracket 60 is provided with an injection nozzle 105 for emitting a jet of water to wash away the urine and the stools remaining in the urination and defecation container 82 in the downstream direction. Adjacently provided near the injection nozzle 105 is an air supply nozzle 205 for drying the lower surface of the buttocks and the lumbar part of the patient.

As shown in FIG. 9, the dead end of the urination and defecation container 82 on the downstream side is provided with a discharge port 102a adapted to discharge urine and stools remaining in the urination and defecation container 82 to an external storage tank 300 through the discharge pipe 103.

As shown in FIGS. 9 and 12, the washing nozzle retainer 61 is provided with a washing nozzle 203, a bidet nozzle 202 and a drying nozzle 204 which are designed to send water or air toward the private parts and the anus of the patient.

Figure 10:
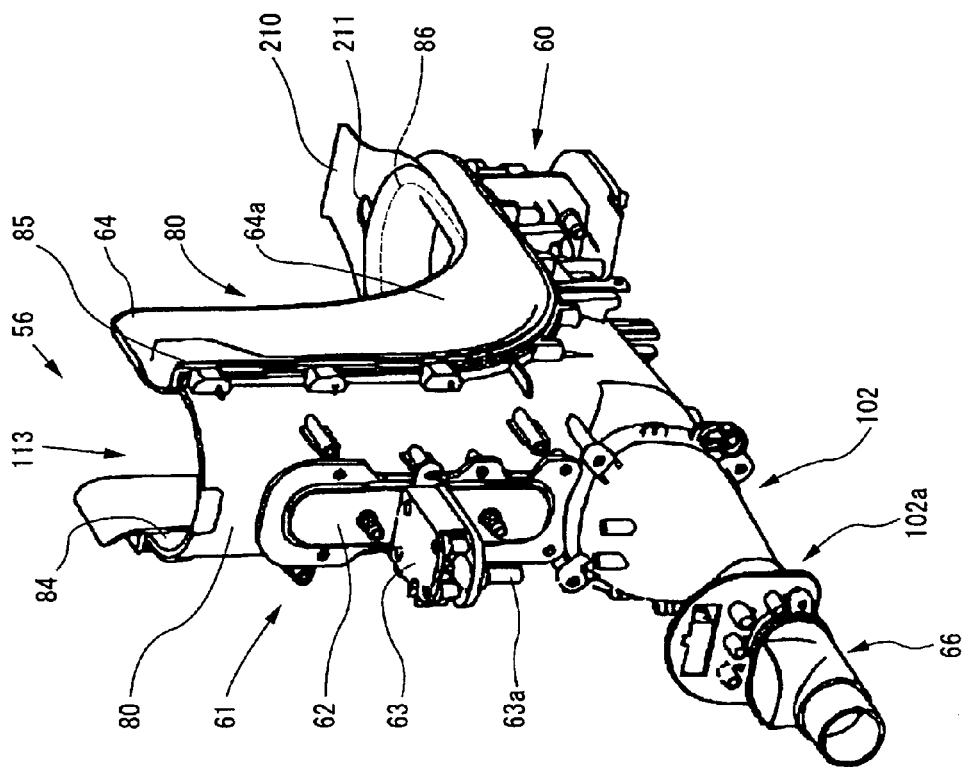
FIG. 10 is a perspective view of a treating body.

A pipe rear anchor leading to each nozzle protrudes, as shown in FIGS. 8 through 10, from the reverse side of the washing nozzle retainer 61 and communicates with a required branch pipe 62a of a distributor 62 attached to the reverse side of the washing nozzle retainer 61. On the reverse side of the distributor 62, a heater section 63 is mounted on the upper surface of the washing nozzle retainer 61 serving as the vertical member of the treating body 56, wherein an air pipe in communication with the distributor 62 is heated through the heater section 63.

The heater section 63 is provided with a suction port 63a and an injection port 63b (refer to FIG. 8). Air sent from the suction port 63a is heated by the air pipe and sent as warm air through the injection port 63b. The suction port 63a of the heater section 63 is communicatively connected to a drying nozzle pipe 608 adapted to ventilate air sent from a suction pump 400, while the injection port 63b of the heater section 63 is communicatively connected to an air supply opening on the obverse side of the distributor 62. In this manner, air sent from the suction pump 400 is heated and provided to the private parts of a human body from the drying nozzle 204 as a comfortable warm current of air for drying.

As shown in FIGS. 8 through 10, an opening section 83 of the treating body 56 and a nozzle projecting side of the washing nozzle retainer 61 are formed to face each other by the urination and defecation container 82 formed in a boat shape and the washing nozzle retainer 61 provided upright on the downstream side of the urination and defecation container 82. Accordingly, an opening edge 84 of the treating body 56 and a side edge of the washing nozzle retainer 61 form an uninterrupted side edge section 85 of a substantially L-shape as seen from the side.

The right and left side edge sections 85, 85 are caused to integrally continue inclusive of a front edge section 86 of the urination and defecation container 82 to have a combined L and U-shape, which serves as a body contacting edge section. In a condition in which the patient holds the urination and defecation treating unit 51 in the crotch of his legs, the crotch and buttocks closely contact the body contacting edge section to keep the inside of the urination and defecation container 82 and the washing nozzle retainer 61 in a highly airtight condition. For that purpose, the body contacting edge section is therefore covered by an edge cover 64 which combines the L-shape with the U-shape to cover the edge section.

In other words, the edge cover 64 is provided to form the continuous lower end surface of the edge section in a depressed shape and is made of synthetic resin to be fitted into the body contacting edge section. The surface of the edge cover 64 is covered by urethane coated with body-friendly resin. Reference numeral 210 is a tongue piece extended at the front end of the edge cover 64. When the edge cover 64 is fitted to the body contacting edge section, the tongue piece 210 is situated to overlap the butt-pad 41 disposed on its periphery. With this provision, the patient does not have stimulus and an uncomfortable feeling on the boundary between his buttocks and the tongue piece 210.

Figure 11:
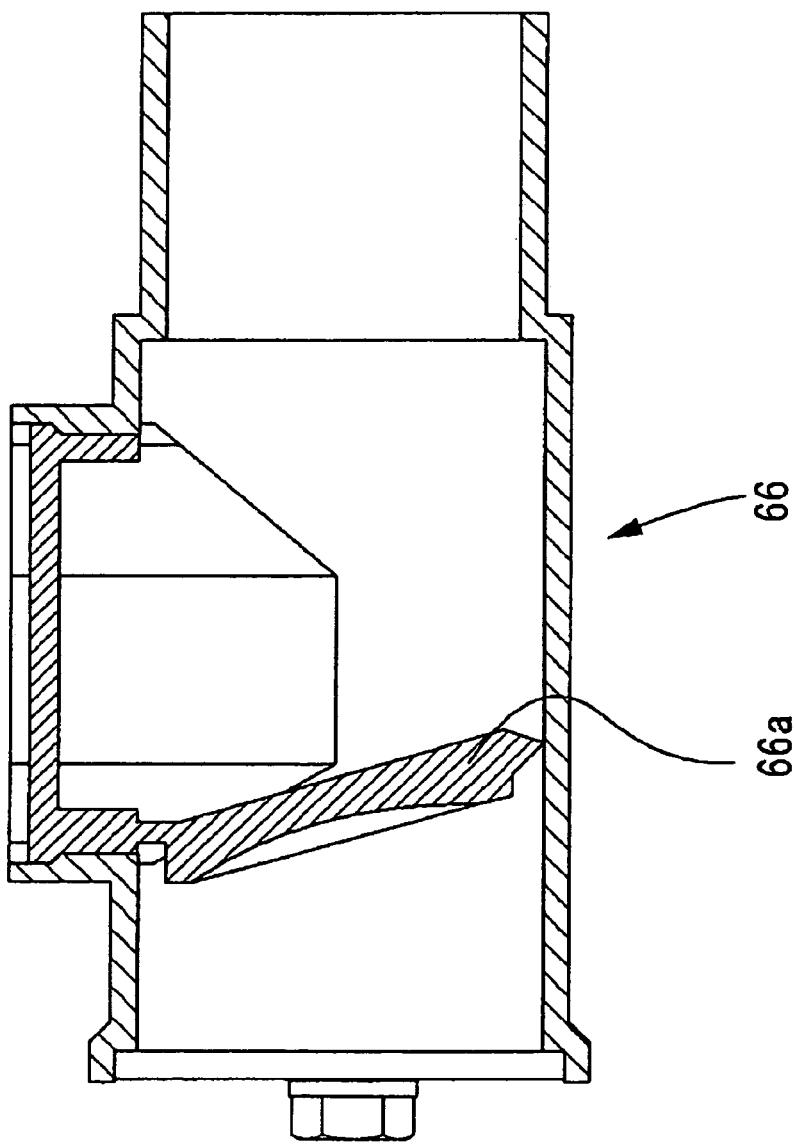
FIG. 11 is a cross-sectional view of a one-way valve casing.

As shown in FIGS. 8 and 9, a hollow one-way valve casing 66 of an octagonal shape in cross-section is installed between the discharge port 102a of the urination and defecation container 82 and the rear anchor side of the discharge pipe 103 to prevent the excretory substance and a foul odor from flowing back. The one-way valve casing 66 (refer to FIG. 11) is vertically provided with a backflow prevention valve 66a of which the upper end is pivotally supported on the ceiling surface of the valve casing 66 to be openable and closable. The backflow prevention valve 66a is always biased in the valve-closing direction by its own weight. The excretory substance such as urine and stools goes into circulation more smoothly with circulating force against the valve's bias by its own weight, while the foul odor from the storage tank 300 and the discharge pipe 103 is prevented from inflowing by the valve closure.

Further, as shown in FIG. 9, a substantially central section of a bottom surface of the support casing 55 is projectingly provided with an engaging hook 67 of a chevron shape in cross section. The downstream section of the bottom surface within the guide passage 34 of the U-shaped casing 31 into which the support casing 55 is fitted is provided with multi-stage engaging grooves 68 (refer to FIG. 5) of a chevron shape in cross section. In the case where the support casing 55 is fitted into the guide passage 34 in a sliding manner toward the front direction from behind, by the engagement of the engaging hook 67 with the engaging grooves 68, it is possible to prevent the treating body 56 within the support casing 55 from being inserted too far into the fork of the patient's legs and to secure the fitting position of the urination and defecation treating unit 51 and the femoral region of the patient in the longitudinal direction in an optimum close contacting location, and to always improve the degree of contact between the urination and defecation treating unit 51 and the femoral region of the patient. In the case where the patient has a feeling of oppression when he holds the urination and defecation treating unit 51 in the crotch of his legs, the engaging hook 67 can be disengaged from the engaging grooves 68 by lifting the urination and defecation treating unit 51 upwards. By sliding the treating body 56 along the guide passage 34 to fine adjust the engaging position of the engaging hook 67 in the backward position of the guide passage 34, it is possible to cause the engaging hook 67 to engage the engaging grooves 68 to bring it into an optimum engaging position and as a result, the patient's oppressed feeling can be reduced. In the case where the urination and defecation treating unit 56 is removed from the patient, the engaging hook 67 of the urination and defecation treating unit 51 is disengaged from the engaging grooves 68 by lifting the urination and defecation treating unit 51 upwards and the urination and defecation treating unit for 51 can be readily removed from the patient.

Installed between the upstream side within the guide passage 34 of the U-shaped casing 31 and the bottom surface of the support casing 55 on the upstream side are a substantially Z-shaped leaf spring 71 and a substantially semi-circular push-up backing plate 72 mounted on the leaf spring 71 for pushing up the bottom surface of the urination and defecation treating unit 51 on the upstream side. In other words, the push-up backing plate 72 is provided on a flat section of the upper surface of the leaf spring 71, and the downstream edge section of the push-up backing plate 72 is pivotally attached to the guide passage 34. With this arrangement, the push-up backing plate 72 is biased upwards by the leaf spring 71 with a central focus on the pivotally attached section. By such biasing force of the leaf spring 71, the urination and defecation treating unit 51 is lifted from the guide passage 31 through the support casing 55 to be pushed against the femoral region of the patient for close contact. Further, the upstream side of the urination and defecation treating unit 51 can be always declined from the upstream side to the downstream side by the push-up backing plate 72. This is effective in capably collecting the excretory substance and the wash water from within the urination and defecation container 82 and discharging them through the discharge port 102a.

(v) Various nozzles and sensors of the urination and defecation treating unit 51 will now be described.

As shown in FIGS. 1 and 9, the urination and defecation treating unit 51 is provided in various places with a buttocks nozzle 104, an injection nozzle 105, a bidet nozzle 202, and a washing nozzle 203 which are adapted to emit a jet of wash water to wash each region of the human body, and a drying nozzle 204 and an air supply nozzle 205 which are adapted to inject air to dry the private parts and external buttocks of the human body after washing. The urination and defecation treating unit 51 is also provided in various places with a fitting sensor I, a stool sensor G, a urine sensor H, and a water level sensor J which are adapted to detect that the femoral region of the human body has contacted the urination and defecation treating unit 51 and to detect human waste such as stools discharged within a discharge passage 81 to detect that defecation has been performed, and to perform various control operations through subsequent electric control, for example, operations such as emission of wash water from various nozzles such as the buttocks nozzle 104, the injection nozzle 105, the bidet nozzle 202, and the washing nozzle 203 and discharge of the human waste.

In this manner, referring to the urination and defecation treating unit 51, the treating body 56 is provided with various nozzles such as the buttocks nozzle 104, the injection nozzle 105, the bidet nozzle 202, and the washing nozzle, and various sensors such as the fitting sensor I, the stool sensor G, the urine sensor H, and the water level sensor J. Various nozzles such as the buttocks nozzle 104, the injection nozzle 105, the bidet nozzle 202, and the washing nozzle 203 and various sensors such as the fitting sensor I, the stool sensor G, the urine sensor H, and the water level sensor J are exposed within the urination and defecation treating unit 51. Various sensors such as the fitting sensor I, the stool sensor G, the urine sensor H, and the water level sensor J will be described hereunder.

(v-1) Various nozzles will now be described in detail.

As shown in FIGS. 9 and 12, the urination and defecation treating unit 51 is provided with the washing nozzle 203 disposed at the lower end section of the bottom surface of a front surface depressed section 113 and the bidet nozzle 202 disposed in a position of the bottom surface of the front surface depressed section 113 higher than the washing nozzle 203. The urination and defecation treating unit 51 is also provided with the injection nozzle 105 disposed at an end section of the discharge passage 81 on the opposite side of a discharge section 102 and the buttocks nozzle 104 disposed in a higher position than the injection nozzle 105 at the end section of the discharge passage 81 on the opposite side of the discharge section 102 and. As shown in FIG. 1, the buttocks nozzle 104, the injection nozzle 105, the bidet nozzle 202, and the washing nozzle 203 are connected to a buttocks nozzle pipe 602c, an injection nozzle pipe 604, a bidet nozzle pipe 602b, and a washing nozzle pipe 603, respectively. Thus, wash water is respectively supplied from a processing operating section C to various nozzles such as the buttocks nozzle 104, the injection nozzle 105, the bidet nozzle 202, and the washing nozzle 203 through each nozzle pipe of the buttocks nozzle pipe 602c, the injection nozzle pipe 604, the bidet nozzle pipe 602b, and the washing nozzle pipe 603.

These various pipes are tied in a bundle and inserted into an external hose 73 (refer to FIG. 8). One end of the external hose 73 is communicatively connected to the end section of the discharge section 102 of the urination and defecation treating unit 51, while the other end thereof is communicatively connected to the storage tank 300. Such an external hose 73 is provided to protect various pipes inserted therein from the impact and pressure applied from outside and to maintain the shape and function of the various pipes.

As shown in FIGS. 9 and 13, the buttocks nozzle 104 is a nozzle for washing the excretory substance adhering to the buttocks of the patient using wash water. The buttocks nozzle 104 is provided with a plurality of injection ports 104a of which the injection direction is directed toward the buttocks of the patient. The injection ports 104a are disposed in such a manner that each port has a predetermined curvature to correspond to the curved surface of the buttocks. The buttock nozzle 104 is communicatively connected to the bidet nozzle 202 through a three-way valve 74. Both the nozzles 104 and 202 are designed to be capable of simultaneously injecting wash water from the three-way valve 74.

The injection nozzle 105 is a nozzle for performing the treatment of washing away the stools from the discharge passage 81 to the discharge port 102a (hereinafter referred to as "stool crushing treatment"), while crushing the stools to pieces by the injection water pressure of the wash water. The injection nozzle 105 is disposed on a protruding section 60a which protrudes from the inner surface of the front end nozzle bracket 60 while gently curving substantially upwards as seen from the front. The protruding section 60a is provided on the bottom surface side of a front end of the discharge passage 81 lower than the buttocks nozzle 104. The injection nozzle 105 has a plurality of stool crushing injection ports 105a of which the injection direction is directed to the bottom surface of the discharge passage 81 and to the area just below the anus of the human body where the stools are tend to most accumulate. The stool crushing injection ports 105a are provided so that the spray angle is, for example, in the range of 2 to 10 degrees and are designed to inject toward the center of the discharge passage 81 where the stools tend to most accumulate. With this arrangement, the stools accumulated in the center of the discharge passage 81 are first crushed and a flow channel through which the wash water flows toward the discharge section 102 is provided. Accordingly, in the early stage in which injection of wash water is initiated from the injection nozzle 105, it is possible to prevent the condition in which the wash water blocked off by the stools spills out of the discharge passage 81. Further, the injection nozzle 105 is in communication with a pressure pump 600 described later and is designed to inject warm water from a hot water tank 501 through the injection nozzle 105 as wash water at high water pressure.

The bidet nozzle 202 shown in FIGS. 9 and 12 is a nozzle for washing the excretory substance adhering to the private parts of the human body and for washing the urine adhering to the inner periphery of the vertical member of the treating body. The bidet nozzle 202 is formed in a narrow and long protruding shape so that the private parts can be washed irrespective of sex and difference of body type. The bidet nozzle 202 has a plurality of bidet injection ports 202a which are drilled in line and at regular intervals and of which the injection direction is directed to the private parts of the patient. The bidet nozzle 202 also has a plurality of urine injection ports 202b which are drilled at regular intervals on the periphery of a protruding shape so that the injection direction is directed to the inner peripheral surface of the vertical member of the treating body. For example, as shown in FIG. 12, the bidet injection ports 202a are drilled in a lattice shape in 9 lines and in 3 rows. As described above, the bidet nozzle 202 is communicatively connected to the buttock nozzle 104 through the three-way valve 74 and both nozzles 104 and 202 are designed to be capable of simultaneously injecting the wash water from the three-way valve. With this configuration, by injecting wash water from each lattice-shaped port 202a in a surface condition, a wide range of washing is not only possible, but also the injection pressure of the wash water can be controlled to a moderate degree and mild washing to the private parts which are particularly delicate in the human body is possible. The urine injection ports 202b of the bidet nozzle 202 are also provided to simultaneously wash the urine scattered inside the urination and defecation treating unit 51.

As shown in FIGS. 9 and 12, the washing nozzle 203 is a nozzle for washing the excretory substance adhering to the anus and an area around the anus of the patient and is formed in a long, narrow shape to be able to wash the anus and an area around the anus irrespective of the difference of body type by sex. The washing nozzle 203 is situated at a lower position than the bidet nozzle 202 and has a plurality of anus injection ports 203a which are drilled at regular intervals and of which the injection direction is directed to the anus and the area around the anus of the patient. For example, as shown in FIG. 12, each anus injection port 203a is drilled in substantially 4 lines and 3 rows, wherein the upper port in the center row is formed to be higher than the upper ports in the lateral row. The distance between the washing nozzles 203 in the same row is formed to be narrower than the distance between the bidet nozzles 202 in the same row. With this arrangement, it is possible to wash the anus and an area around the anus of the human body irrespective of the difference of body type by sex. Water pressure of the wash water emitted through each anus injection port 203a is designed to be stronger than that of the wash water injected through the bidet injection port 202a.

To realize more effective washing, the stool crushing injection port 105a and the anus injection port 203a can adopt an orifice structure. By adopting the orifice structure, the injection scope of the wash water can be expanded and as a result, it is possible to wash a wide range of human bodies while controlling the volume of the wash water.

Wash water is supplied to the bidet nozzle 202, the washing nozzle 203, the injection nozzle 105, and the buttocks nozzle 104 from the processing operating section C through various nozzle pipes such as the buttocks nozzle pipe 602c, the injection nozzle pipe 604, the bidet nozzle pipe 602b, and the washing nozzle pipe 603. After washing each region of the patient by the wash water, warm air and air blasting are provided to each region through the drying nozzle 204 and the air supply nozzle 205 for drying.

As shown in FIGS. 9 and 12, the drying nozzle 204 is a nozzle for drying the private parts, the anus and an area around the anus of the patient, and is provided in the substantially four corners of the bidet nozzle 202 of a long, narrow shape so that the private parts, the anus, and an area around the anus of the patient can be dried by warm air irrespective of the difference of body type by sex. The drying nozzle 204 is situated further to the outer side than the bidet nozzle 202 and is integrally formed with the bidet nozzle 202. The drying nozzle 204 has four drying injection ports 204a which are drilled at regular intervals of which the injection direction is directed to the private parts, the anus, and the area around the anus of the patient. The drying nozzle 204 is provided in such a manner that, to enable the injection of warm air, air supplied from a suction pump and supplied from the drying nozzle pipe 608 through a solenoid valve 97 (refer to FIG. 1) is heated by a heater of the heater section 63 to discharge warm air from the drying injection port 204a. With this arrangement, it is possible to efficiently dry the private parts, the anus, and an area around the anus of human body with comfortable warm air in a short time irrespective of the difference of body type by sex. For example, two drying injection ports 204a, 204a drilled on the upstream side are provided to inject warm air to the private parts, the anus, and an area around the anus of the human body, while two drying injection ports 204a, 204a drilled on the downstream side are adapted to inject warm air to the anus, an area around the anus, and the buttocks on the upstream side. As a result, it is possible to perform warm air drying efficiently.

As shown in FIGS. 9 and 13C, the air supply nozzle 205 is a nozzle for drying an area sound the buttocks. The air supply nozzle 205 is provided outside a head section of the front end nozzle bracket 60 to provide an upward port to be capable of drying an area around the buttocks and a lumbar region irrespective of the difference of body type by sex. The air supply nozzle 205 has an air supply injection port 205a which turns upward and of which the injection direction is directed to an area around the buttocks of the patient. The air supply nozzle 205 is provided to inject air, which is supplied from a suction pump and supplied from the air supply nozzle pipe 609 through a solenoid valve 98 (refer to FIG. 1), from the air supply injection port 205a. With this arrangement, an area around the buttocks can be efficiently dried in a short time by air blasting irrespective of the difference of body type by sex. For example, air supplied from the air supply injection port 205a is sprayed onto an area around the buttocks through an opening 211 formed on the tongue piece 210 (refer to FIG. 8) to dry, in particular, the buttocks and an area around the lumber region protruding outside the urination and defecation container 82.

(v-2) Structure of various sensors will be described below.

As shown in FIG. 9, the urination and defecation treating unit 51 is provided on the internal surface of the edge cover 64 with the fitting sensor I for detecting that the urination and defecation treating unit 51 has been brought into close contact with the femoral region of the patient at a constant pressure. The urination and defecation treating unit 51 is also provided with a light-emitting section 106 of an infrared sensor at an end section of the discharge passage 81 on the opposite side of the discharge section 102. A light-receiving section 107 of the infrared sensor is provided at the front edge section of the discharge section 102 on the downstream side. The light-emitting section 106 and light-receiving section 107 function as a stool sensor G for detecting stools in the discharge passage 81. The urination and defecation treating unit 51 is further provided with a urine sensor H for detecting the urine at the bottom surface of the urination and defecation container 82 on the downstream side. A water level sensor J for detecting a water level within the urination and defecation container 82 is provided at a side edge section 85 of the urination and defecation container 82 on the upstream side.

The fitting sensor I has a pair of electrode terminals 120 made of conductive rubber and detects that the urination and defecation treating unit 51 has been fitted on the femoral region of the patient by the change of electrostatic capacity peculiar to the human body when both electrodes 120, 120 are brought into close contact with the femoral region of the patient at a constant pressure. Both electrode terminals 120, 120 are disposed to face the internal surface of an L-shaped vertical section of the edge cover 64 and are connected to the processing operating section C through a conductive wire (not shown).

When the femoral region of the patient closely contacts with the edge section of the edge cover 64 at a constant pressure, the edge section curves to be turned up outwards to bring both electrode terminals 120, 120 into close contact with the femoral region. This makes the detection possible. Since the electrode terminal 120 is provided with the conductive rubber, the electrode terminal 120 excels in water proofing property and is effective in enhancing the reliability of the sensor over a long period of time. When the femoral region of the patient is disengaged from the fitting sensor I, injection of the wash water from each nozzle stops. In this manner, it is possible to prevent the mattress 11 and the like around the urination and defecation treating unit 51 from being inundated with wash water and thus, the fitting sensor I is effective in functioning as a safety device. For example, as shown in FIGS. 8 and 9, if the fitting position of both electrode terminals 120, 120 of the fitting sensor I is set several cm higher than an edge rear anchor of the vertical section 64a of the edge cover 64 and near the inner edge section, it is possible to carry out a function for the fitting sensor I which contacts the femoral region at a constant pressure.

As shown in FIG. 9, the stool sensor G detects whether or not there are stools between the light-emitting section 106 and the light-receiving section 107, in other words, in the discharge passage 81, based on whether or not the infrared light emitted from the light-emitting section 106 was received at the light-receiving section 107 facing the light-emitting section 106. The light-emitting section 106 projects in the upper center of the front end nozzle bracket 60 and is installed in a position higher than the central stools crushing injection port 105a of the injection nozzle 105 and in a position in which the wash water of the buttocks nozzle 104 does not hit directly. The light-receiving section 107 is installed at the upper section of the discharge section 102 where the surrounding light does not reach to prevent malfunction caused by the surrounding light other than the infrared light. Since the infrared light emitted from the light-emitting section 106 is blocked off by the stools no mater where the stools exist in the discharge passage 81, the amount of infrared light which is received by the light-receiving section 107 decreases. In this manner, the stool sensor G can detect stools without fail irrespective of the difference of body type of the individual patient, the fitting condition of the urination and defecation treating unit 51 and the amount of stools.

Further, as shown in FIGS. 8 and 9, the urine sensor H is provided with a pair of electrode pins 109, 109 which are adjacently disposed in sequence. The electrode pins 109, 109 are connected to the processing operating section C through a conductive wire (not shown), wherein a gentle electric current is transmitted to one or the other of the electrode pins 109, 109 from the processing operating section C. The urine sensor H is designed to detect the current value in the case where the gentle current is applied between the electrode pins 109, 109 using the wash water or the urine as an electric conductor. Generally, since the wash water and the urine differ in salinity, a difference in electric conductivity is caused. In other words, the current value detected by the urine sensor H differs in the wash water and the urine.

Since the urine has a higher salinity than water, there is a great difference in the urine sensor output value of the urine and water corresponding to this difference of salinity. Accordingly, by detecting the current value between the electrode pins 109, 109 and using a predetermined threshold value for the urine sensor output value, it is possible to surely distinguish between the washing water and the urine.

The electrode pins 109, 109 are plated with gold for corrosion protection and the positive and negative terminals of a voltage applied to one of the electrode pins 109, 109 are provided to cross over. With this configuration, it is possible to prevent one or the other of the electrode pins 109, 109 from being oxidized to corrode with long-term use or to prevent a problem whereby the detection accuracy deteriorates due to the attachment of foreign object.

With such an arrangement, when the patient defecates and/or urinates, the urination and defecation treating unit 51 detects the stools and/or the urine by the stool sensor G and the urine sensor H and the detected signal is sent to the processing operating section C (refer to FIG. 1). The processing operating section C which has received such a detected signal provides the bidet nozzle pipe 602b, the washing nozzle pipe 603, the injection nozzle pipe 604, and the buttocks nozzle pipe 605 with wash water. The wash water is then injected into the urination and defecation treating unit 51 from each nozzle of the bidet nozzle 202, the washing nozzle 203, the injection nozzle 105, and the buttocks nozzle 104. With this, the buttocks section, private parts and the anus of the patient are washed and the urine and stools are washed away toward the discharge section 102. After completing such a washing process for washing each region of the patient and the inside of the urination and defecation treating unit 51, air is sent to the drying nozzle pipe 608 and the air supply nozzle pipe 609 and then warm air and air blasting are injected into the urination and defecation treating unit 51 from the drying nozzle 204 and the air supply nozzle 205. In this manner, a drying process for drying the buttocks section, the private parts and the anus of the patient is executed.

The water level sensor J is provided, as shown in FIGS. 8 and 9, with electrode pins 130, 130 at side edge sections 85, 85 of the urination and defecation container 82 on the upstream side to detect the water level within the urination and defecation container 82. The electrode pins 130, 130 are connected to the processing operating section C through a conductive wire (not shown), wherein a gentle electric current is applied to one or the other of electrode pins 130, 130 from the processing operating section C (refer to FIG. 1). The water level sensor J detects the current value in the case where such a gentle current is applied between the electrode pins 130, 130 using the wash water and the urine as a conductor.

When the water level rises extraordinarily due to the wash water containing excretory substance remaining within the discharge passage 81 and then, both electrode pins 130, 130 go under the wash water, as an electric current is applied between the electrode pins 130, 130, the water level sensor J can detect that the wash water is building up within the urination and defecation container 82 in excess of a predetermined water level. For example, in the case where the injection nozzle 105 is crushing the stools with the wash water, if the water level sensor J has detected that the wash water is building up in the urination and defecation container 82 above the predetermined water level, the processing operating section C stops the injection of wash water from the injection nozzle 105 and forcibly conducts the sucking operation of, preferentially, the wash water containing urination, defecation and the like from the discharge port 102a of the urination and defecation container 82 into the storage tank 300 through the discharge pipe 103.

(vi) The urine collecting device will now be described.

Figure 14A:
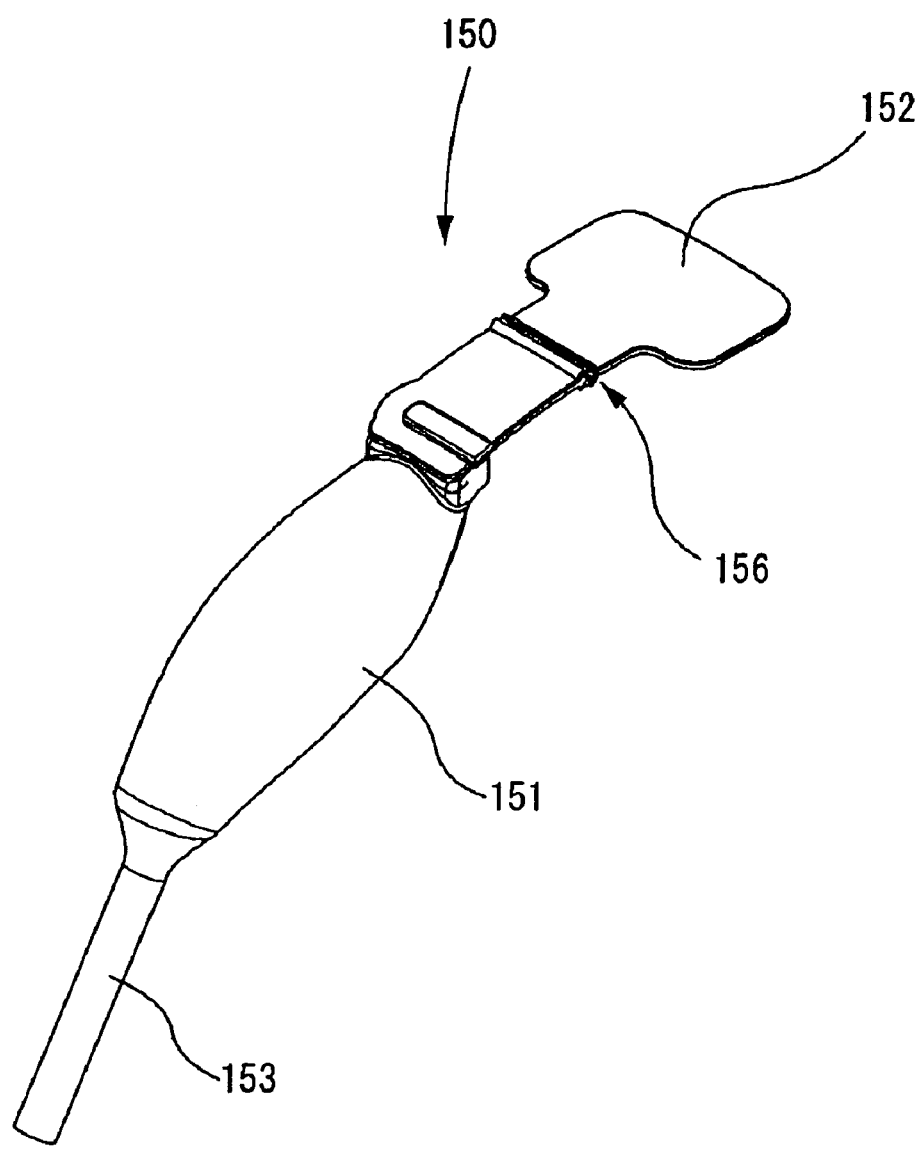

FIG. 14 shows a urine collecting device 150 which is used in the implementation of an automatic treating device K for urination and defecation according to the present invention. The urine collecting device 150 can also be used as a stand-alone device when a man urinates. The urine collecting device 150 comprises a urine collecting body 151 of a curved cylinder shape, an attaching section 152 of a flat plate shape provided at the rear anchor of the urine collecting body 151, and a urine flow pipe 153 provided at the front end of the urine collecting body 151.

The urine collecting body 151 is formed in a bag shape made of silicone consisting of the private parts inserting section 154 of which the leading edge is obliquely opened and a urine collecting space section 155 formed in a curved cylinder shape. The urine collecting body 151 is provided in such a manner that a man can insert his private parts into the urine collecting space section 155 through the private parts inserting section 154 and urinate within the urine collecting space section 155. Thus, the urine collecting body 151 is formed in the curved-shape bag made of silicone and the private parts inserting section 154 is composed of an opening edge obliquely cut away in the downward direction. In this manner, the urine collecting body 151 can be displaced or deformed in a position corresponding to the male urinating direction from his private parts. The urine collecting body 151 thus can correspond to the male sex organ's physiologic displacement, that is, the bodily changes such as erection, expansion and contraction.

The attaching section 152 is provided to project in a flat plate shape at the upper edge section of the leading edge of the urine collecting body 151 and its reverse side can be detachably affixed to an abdominal seam location of the patient's diaper 21 using a taper and the like. The attaching location of the attaching section 152 is arbitrarily adjustable. A hinge section 156 is provided in the middle of the attaching section 152 to be foldable or pivotable. The attaching section 152 can be folded in response to the vertical displacement of the urine collecting body 151 to be fitted to the private parts of the patient. The attaching section 152 and the urine collecting body 151 are foldably provided depending upon the body type of the patient. The silicone material of the urine collecting body 151 contains a negative ion generating material to remove bad odors and can contribute to ion reforming in the constitution of the patient. The urine flow pipe 153 is a short pipe communicatively connected to a dead end of the urine collecting body 151 and the pipe direction can be guided manually. The urine flow pipe 153 can be guided manually into the urination and defecation treating unit 51 of the automatic treating device K for urination and defecation according to the present invention to discharge urine therein.

(vii) The processing operating section C as an external processing structure will be described below.

The processing operating section C is provided outside the urination and defecation treating unit 51 to carry out various functions for treating urination and defecation. As shown in FIG. 1, the processing operating section C is composed of an excretory substance housing section D for housing human waste from the urination and defecation treating unit 51, a nozzle operating section F for receiving a fitting signal which shows a close contact condition between the crotch of the patient's legs and the urination and defecation treating unit 51 at a constant pressure, a detection signal of defecation and/or urination, and a water level signal showing the water level rising in the urination and defecation container, and for performing subsequent various operations such as a washing operation, and a wash water supply section E for supplying the urination and defecation treating unit 51 with wash water.

(vii-1)

The excretory substance housing section D has a storage tank 300. The storage tank 300 is connected to the discharge port 102a of the urination and defecation treating unit 51 through the discharge pipe 103. The storage tank 300 can be removed from the processing operating section C when the waste material contained therein is disposed of. The bottom section of the storage tank 300 is provided with a weight sensor 302 for detecting the weight of waste material stored therein. The weight sensor 302 sends a signal to the processing operating section C when exceeding the predetermined weight.

As shown in FIG. 1, a suction pipe 401a is connected to a hose connecting section 303 to be adjacent to the discharge pipe 103. As shown in FIG. 1, the storage tank 300 is connected to the nozzle operating section F through the suction pipe 401a. The inside of the storage tank 300 is provided in such a manner that air is sucked through the suction pipe 401a by the actuation of the suction pump 400 in the nozzle operating section F described below to provide a negative pressure condition and the waste material can be sucked from the urination and defecation treating unit 51 through the discharge pipe 103.

(vii-2)

The wash water supply section E comprises, as shown in FIG. 1, a raw water tank 500 for supplying raw water serving as the wash water, a hot water tank 501 for heating the wash water supplied into the urination and defecation treating unit 51 to a predetermined temperature, and a solenoid valve 503 for controlling water supply from the raw water tank 500 to the hot water tank 501. The hot water tank 501 is composed of a pipe heater 502 for heating the raw water supplied from the raw water tank 500 through the solenoid valve 503, a water level sensor 505 for detecting water level, and a temperature sensor 506 for detecting the water temperature. The wash water supply section E is provided in such a manner that, when the water level sensor 505 detects that the water level within the hot water tank 501 is in a condition in which water supply is needed, the solenoid valve 503 is opened to supply a predetermined amount of raw water to the hot water tank 501 from the raw water tank 500, and when the water level sensor 505 detects that the hot water tank 501 is filled with the raw water to reach a predetermined water level, the solenoid valve 503 is closed based on the detection signal of the water level sensor 505 to shut off the supply of raw water.

In the wash water supply section E, in order to detecting the temperature of the raw water within the hot water tank 501 by the temperature sensor 506 to maintain the temperature which the patient set through a temperature control circuit (not shown), the raw water is heated by the pipe heater 502 to get warm water. With this configuration, in the case where a washing process for supplying the urination and defecation treating unit 51 with warm water in the hot water tank 501 as the wash water is executed, the wash water of a desired temperature is always supplied to the patient and as a result, the patient can get a favorable use condition. An outlet provided on the side surface of the bottom section of the hot water tank 501 is connected to the nozzle operating section F through the water supply pipe 504a and the wash water heated within the hot water tank 501 is supplied to the nozzle operating section F through the water supply pipe 504a.

It is also possible to adjust the supply of raw water from the raw water tank 500 to the hot water tank 501 by using a float valve and the like in place of the solenoid valve 503.

(vii-3)

The nozzle operating section F is connected, as described above, to the excretory substance housing section D through the suction pipe 401a and is connected to the wash water supply section E through the water supply pipe 504a. The suction pipe 401a is connected to a suction port 402 of a suction pump 400 through a suction valve 409 as a valve, a vacuum tank 408 as a pressure reducing section, a suction pipe 401b, a bad odor eliminating filter 407a, a pressure switch 413, a suction pipe 401c, a NO port of a solenoid valve 96, a COM port of the solenoid valve 96, and a suction pipe 401d. A discharge port 405 of the suction pump 400 is connected to a COM port of a solenoid valve 95, and a NO port of the solenoid valve 95 is connected to a silencer 407b through an air discharge pipe 414. The silencer serves as an air supply port and an exhaust port.

On the other hand, the water supply pipe 504a is connected to the buttocks nozzle 104, the injection nozzle 105, the bidet nozzle 202, and the washing nozzle 203 within the urination and defecation treating unit 51 through a filter 507, a water supply pipe 504b, a pressure pump 600, a nozzle pipe 601a, various solenoid valves such as 91, 92, 93, a three-way valve 74, and various nozzle pipes such as 602a, 602b, 602v, 603, and 605. In other words, by pressurizing the wash water supplied from the wash water supply section E with the pressure pump 600, the wash water can be injected into the urination and defecation treating unit 51 from various nozzles such as the buttocks nozzle 104, the injection nozzle 105, the bidet nozzle 202, and the washing nozzle 203. In order to prevent the pressure pump 600 from receiving foreign objects, the filter 507 is designed to be capable of eliminating foreign objects mixed in the wash water.

However, it is difficult to completely suck and house the human waste pooled within the urination and defecation treating unit 51 in the storage tank 300 only by the suction force of the suction pump 400. Consequently, the vacuum pump 408 for increasing the suction force of the suction pump 400 is disposed between the suction pump 400 and the storage tank 300. By providing the vacuum condition within the vacuum tank 408, intense negative pressure is caused to generate to be capable of efficiently sucking the waste material housed within the urination and defecation treating unit 51.

The exhaust port 405 of the suction pump 400 is connected to the COM port of the solenoid valve 95 and the NC port of the solenoid valve 95 is connected to the drying nozzle 204 and the air supply nozzle 205 within the urination and defecation treating unit 51 through the air supply pipe 601b, various solenoid valves such as 97 and 98, and various nozzle pipes such as 608 and 609.

On the other hand, provided on the suction port 402 side of the suction pump 400 is a silencer 404 which is connected to the NC port of the solenoid valve 96 through an external air supply pipe 415. The COM port of the solenoid valve 96 is connected to a suction port 402.

In the nozzle operating section F, various solenoid valves 91, 92, and 93 for water supply, and various solenoid valves 97 and 98 for air supply are combined to provide a solenoid valve unit 606 forming a pipe channel by one inflow port and four outflow ports. The solenoid valve unit 606 is designed to be capable of selectively opening and closing the four outflow ports in order through a control circuit (not shown). With this configuration, it is possible to simplify the pipe channel structure to reduce the number of parts, and to increase the assembly efficiency.

Further, the solenoid valves 95, 96, the silencer 404, two units of bad odor eliminating filters 407a, 407a, and the silencer 407b are combined to provide a filter assembly 607. With this arrangement, it is possible not only to simplify the pipe channel formation to reduce the number of parts, but also to increase the assembly efficiency and to make the replacement operation of the silencer 404, various filters 407a, 407a, and the silencer 407b easy.

(viii) The flow of the procedures and functions in the case where the toilet unit A for use in a supine position according to the present embodiment is used will be described. The process of urination and defecation treatment will be described. The usage of the urination and defecation treating unit 51 will also be described below.

First, a diaper 21 is put on a depressed section 12 of a mattress 11. In a condition in which the toilet unit A for use in a supine position is fitted onto the mattress 11 according to the fitting procedure of the diaper 21 described in (i), the crotch of the legs and private parts of the patient are covered. In this case, the patient is in a condition in which he holds the washing nozzle retainer 61 which is a vertical casing 53 of the toilet unit A in the fork of his legs, wherein the patient's buttocks are mounted on a butt-pad 41 and his private parts are brought to face the urination and defecation container 82 of a lateral casing 52. In such a condition, the patient urinates and defecates within the urination and defecation container 82 and then, the following urination and defecation treatment is carried out.

As a treating pattern of the automatic treating device K for urination and defecation, there are two modes of an automatic defecation treating mode for automatically conducting each washing process by distinguishing the stools and urine based on the detection of the stool sensor G and the urine sensor H, and a manual defecation treating mode for conducting each washing process when instructed by the patient. There are a stool washing process, a urine washing process, and a drying process in the automatic defecation treating mode and each process will be described in order according to each flow chart. The automatic treating device K for urination and defecation is provided with a control section for controlling various nozzles, each sensor, various valves, each pump and the like. The control section sends signals to various nozzles, various valves, each pump and the like based on the signal of each sensor to execute various functions.

Figure 15:
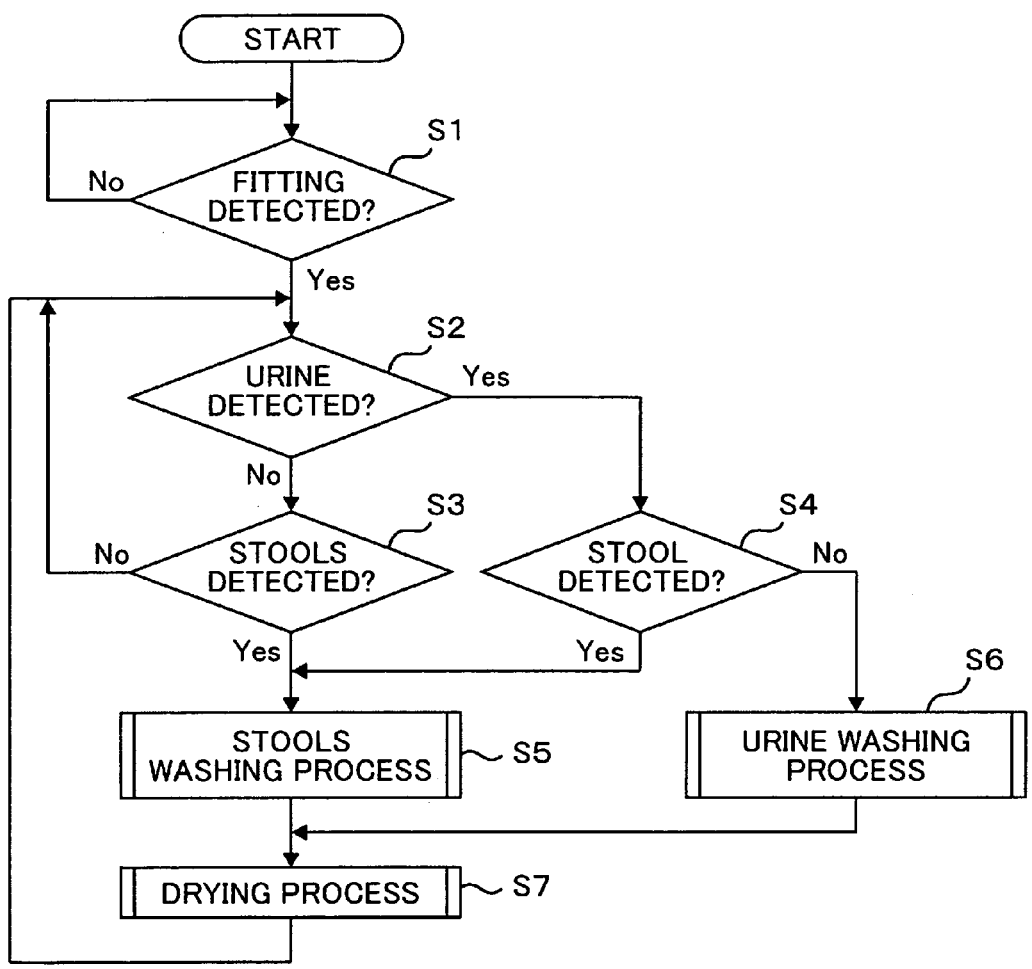
FIG. 15 is a flow chart showing the steps of a procedure of the automatic treating device for urination and defecation in an automatic defecation treating mode.

(viii-1) FIG. 15 is a flow chart for showing the steps of a procedure of the automatic treating device K for urination and defecation in the automatic defecation treating mode.

As shown in FIG. 15, when power is applied to a main body by the operation of a power switch (not shown), a judgment is made as to whether or not a crotch of a patient's legs has come into close contact with both electrode terminals 120, 120 at a constant pressure based on the detection signal of the fitting sensor I (Step S1). As a result of this judgment, in the case where the crotch of the patient's legs has closely contacted the electrode terminals 120, 120 at a constant pressure (Step S1: Yes), a program proceeds to the following Step S2 in which it is judged whether or not the urine exists in a discharge passage 81 based on the detected value of a urine sensor H. In the case where the crotch of the patient's legs has not closely contacted the electrode terminals 120, 120 at a constant pressure (Step S1: NO), the judgment as to whether or not the crotch of the patient's legs has closely contacted the electrode terminals 120, 120 is repeated.

As a result of this judgment, if the urine does not exist (Step S2: NO), it is judged whether or not stools exist in the discharge passage 81 based on the detection value of a stool sensor G (Step S3). As a result of this judgment, if the stools do not exist (Step S3: NO), the program returns to Step S2 to judge again whether or not the urine exists. On the other hand, if stools exist (Step S3: YES), in other words, if only stools exist in the discharge passage 81, a stool washing process is executed (Step S5).

In Step S2, if urine exists (Step S2: YES), it is judged whether or not stools exist in the discharge passage 81 (Step S4). As a result of this, if stools exist (Step S4: YES), in other words, if urine and stools exist in the discharge passage 81, the stool washing process for treating the stools is executed (Step S5).

On the other hand, if stools do not exist (Step S4: NO), in other words, if only urine exists in the discharge passage 81, a urine washing process for treating the urine is executed (Step S6).

After the stool washing process (Step S5) or the urine washing process (Step S6) is completed, the automatic treating device K for urination and defecation executes a drying process for drying a human body and the inside of the urination and defecation treating unit 51 (Step S7).

Figure 16A:
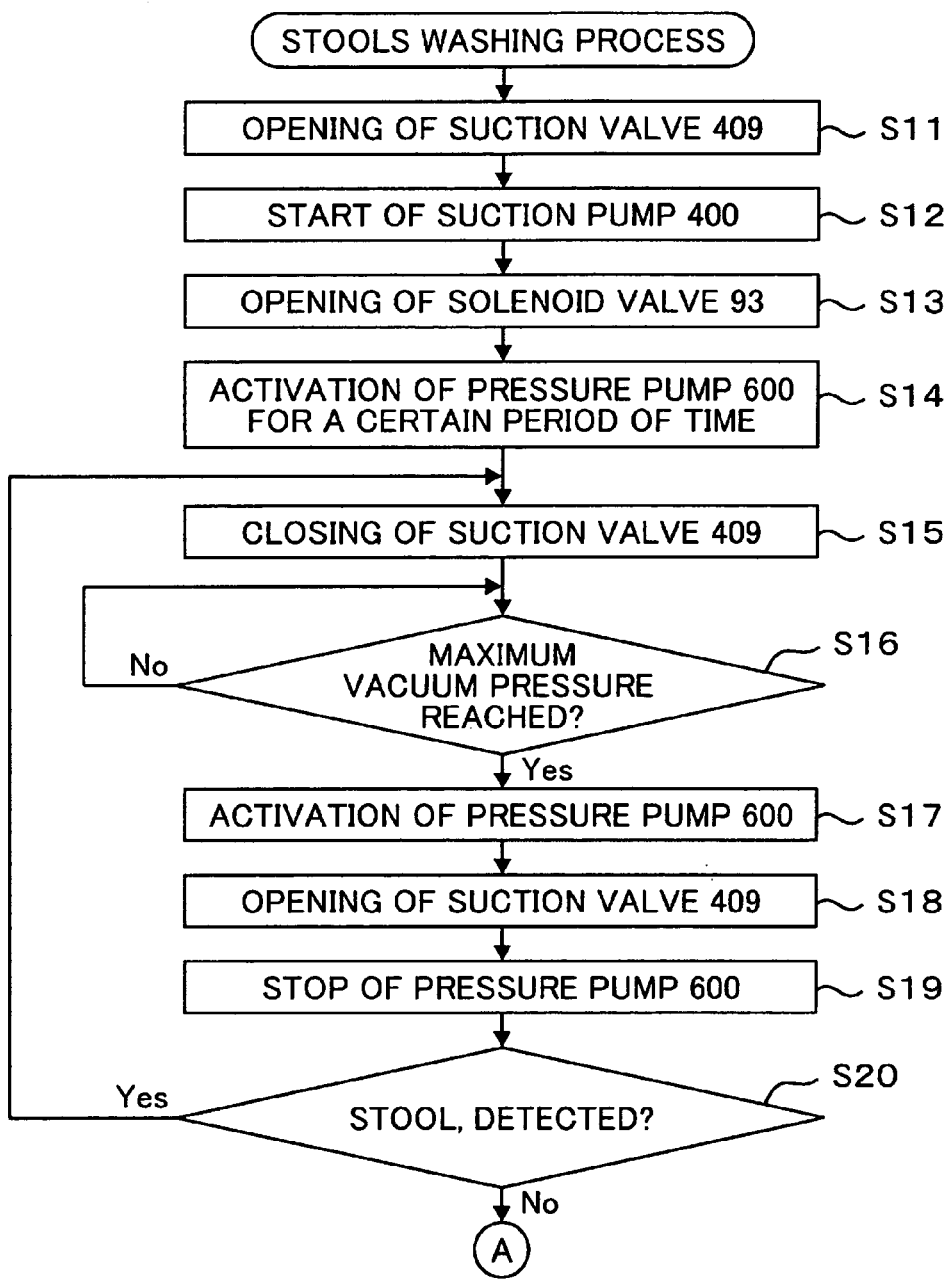
FIG. 16 is a flow chart showing the steps of a procedure of a stool washing process.
Figure 16B:
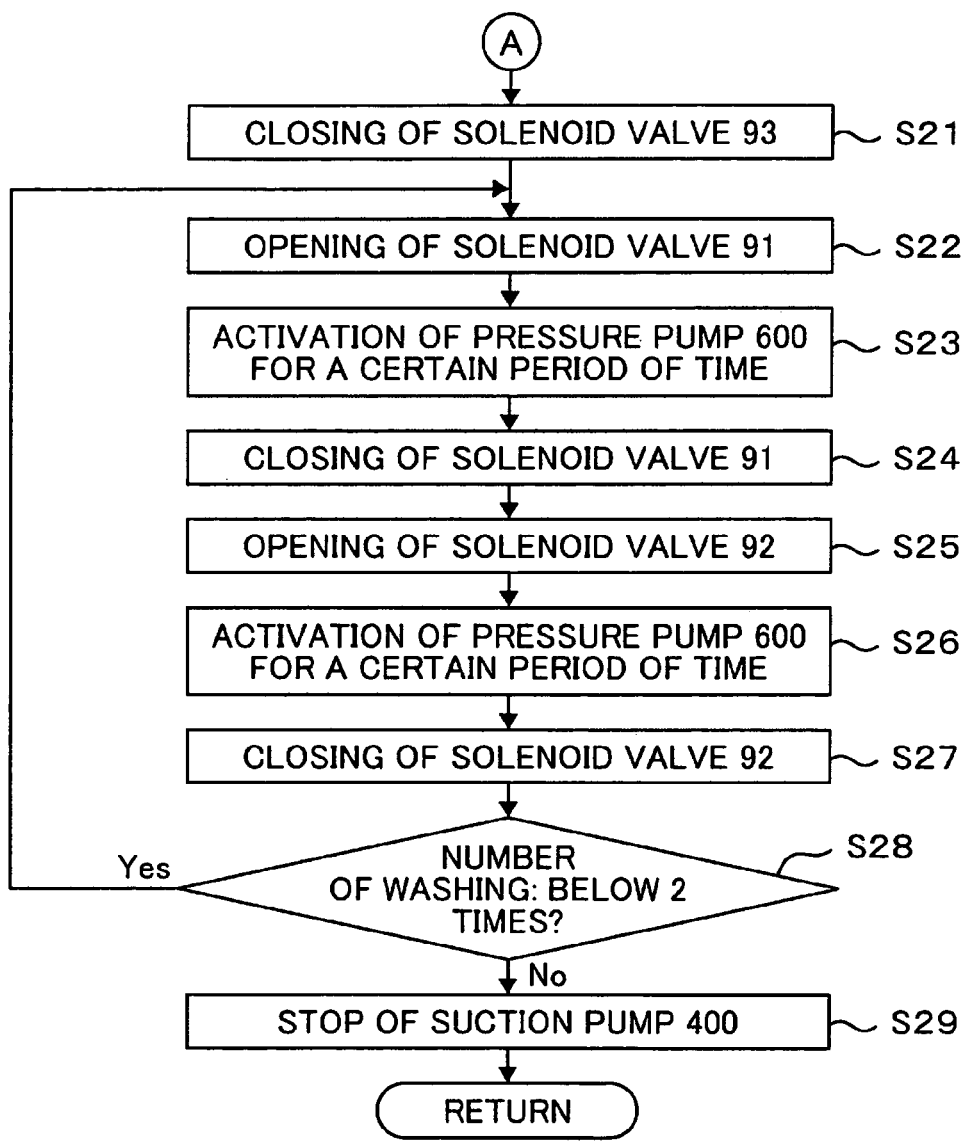

(viii-2) FIG. 16 is a flow chart showing the steps of a procedure, of the stool washing process.

In the initial condition, various solenoid valves 91 through 93, the NC ports of the solenoid valves 95, 96, the suction valve 409, and the one-way valve 411 are closed. Also, in the initial condition, the NO ports of the solenoid valves 95, 96 are opened. As shown in FIG. 16, first, the suction valve 409 is opened (Step S11) and the suction pump 400 is activated (Step S12). With this operation, bad odor due to the stools within the urination and defecation treating unit 51 and part of the stools are sucked into the storage tank 300. Simultaneously, air containing the bad odor within the urination and defecation treating unit 51 flows toward the one-way valve casing 66, the discharge pipe 103, the storage tank 300, and the suction pump 400, wherein the bad odor is eliminated through a bad odor eliminating filter 407a before the suction port 402 and the silencer 407b after the exhaust port 405 before being emitted outside. In the case where the air is emitted outside, the sound can be muffled with a provision of the silencer 407b. Since two units of the bad odor eliminating filters 407a, 407a are communicatively connected to each other in parallel, it is possible to maintain the bad odor eliminating effects for a long time.

Next, after the solenoid valve 93 is opened (Step S13), the pressure pump 600 is actuated for a certain period of time (Step S14). With this, the warm water within the hot water tank 501 is sent to the injection nozzle pipe 604 and is injected as wash water from the injection nozzle 105 to execute the stool crushing operation. The stools crushed by the stool crushing treatment are pushed away in the direction of the discharge passage 81 and mixed well with the wash water in a waste storage space S by a turbulence phenomenon (hereinafter referred to as "mixing operation due to turbulence phenomenon"). When the wash water is injected from the injection nozzle 105, the water level sensor J detects whether or not the water level within the urination and defecation container 82 is above a certain level. If the water level is above the certain level, the water level sensor J forcibly stops the injection from the injection nozzle 105 and causes the waste substance within the urination and defecation container 82 to be sucked through the discharge pipe 103 and stored in the storage tank 300.

Next, in order to evacuate air from the vacuum tank 408, the suction valve 409 is closed to initiate vacuum forming operation (Step S15). After waiting until the detected value of internal pressure based on a pressure switch 413 reaches the maximum vacuum pressure (e.g., 600 mmHg) (Step S16:

YES), a pressure pump 600 is activated through a control device (not shown) based on the detection signal from the pressure switch 413 (Step S17) and the suction valve 409 is opened (Step S18). At this moment, by the maximum vacuum pressure formed in the vacuum tank 408, the flow of wash water containing the stools is interrupted in the urination and defecation container 82 and the turbulent phenomenon is caused whereby the wash water containing the stools is whirled round vertically to produce a swirling flow. In this manner, the stools after the mixed operation are crushed into pieces to be mixed well with the wash water. Simultaneously, an area, in particular, near the discharge section 102 within the urination and defecation treating unit 51 where the human waste tends to adhere is washed sufficiently to be sucked and housed at a stretch within the storage tank 300 through the discharge section 102, the one-way valve casing 66, and the discharge pipe 103 (hereinafter referred to as "vacuum suction operation"). Since the backflow prevention valve 66a opens against its own weight during suction of stools, the one-way valve casing 66 is provided to suck and house stools and foul odor. After suction is over, the backflow prevention valve 66a closes by its own weight to shut off the stools and the foul odor. In this manner, the sanitary conditions within the urination and defecation treating unit 51 can be improved at any time.

Then, the pressure pump 600 is stopped (Step S19) and it is judged again whether or not residual stools exist within the discharge passage 81 based on the detected value of the stool sensor G (Step S20). As a result of this, if residual stools exist (Step S20: YES), the program returns to Step S15 to repeat the mixing operation due to the turbulence phenomenon and the vacuum suction operation. The mixing operation due to the turbulence phenomenon and the vacuum suction operation are repeated until the stool sensor G stops detecting stools.

When residual stools are no longer detected within the discharge passage 81 (Step S20: NO), the solenoid valve 93 is closed (Step S21). Next, the solenoid valve 91 is opened (Step S22) and the pressure pump 600 is activated for a certain period of time (Step S23). With this, warm water from the hot water tank 501 is sent to the pipe 602a, wherein the warm water is then sent to the bidet nozzle pipe 602b and the buttocks nozzle pipe 602c by the three-way valve 74. On the one hand, the warm water sent to the bidet nozzle pipe 602b is injected from the bidet nozzle 202 as wash water to wash the stools adhering to an area near the private parts of the patient (hereinafter referred to as "bidet washing operation"). On the other hand, the warm water sent to the buttocks nozzle pipe 602c is injected as wash water from the buttocks nozzle 104 to wash away the stools adhering to an area near the buttocks of the patient (hereinafter referred to as "buttocks washing operation"). In this case, it is possible to reduce the washing time since the bidet washing and the buttocks washing can be executed at the same time.

Next, the solenoid valve 91 is closed (Step S24). Then, the solenoid valve 92 is opened (Step S25) and the pressure pump 600 is activated for a certain period of time (Step S26). In this manner, the warm water from the hot water tank 501 is sent to the washing nozzle pipe 603, wherein the warm water is injected from the washing nozzle 203 as wash water to wash away the stools adhering to an area near the anus of the patient (hereinafter referred to as "anus washing operation"). The solenoid valve 92 is closed (Step S27) and the buttocks washing operation and the anus washing operation are repeated until the number of washings reaches two times (Step S28: YES). With this, it is possible to perfectly execute washing an area near the buttocks and the anus of the patient.

Next, when the number of washings reaches two times (Step S28: NO), the suction pump 400 is stopped (Step S29) and the suction valve 409 is closed to complete the stool washing process. In the stools washing process, when the wash water is injected from the various nozzles, the water level sensor J always detects whether or not the water level within the urination and defecation container 82 is above a certain level. If the water level is above a certain level, the water level sensor J forcibly stops the injection of wash water from the various nozzles to cause the human waste within the urination and defecation container 82 to be forcibly sucked through the discharge pipe 103 and housed in the storage tank 300.

Figure 17:
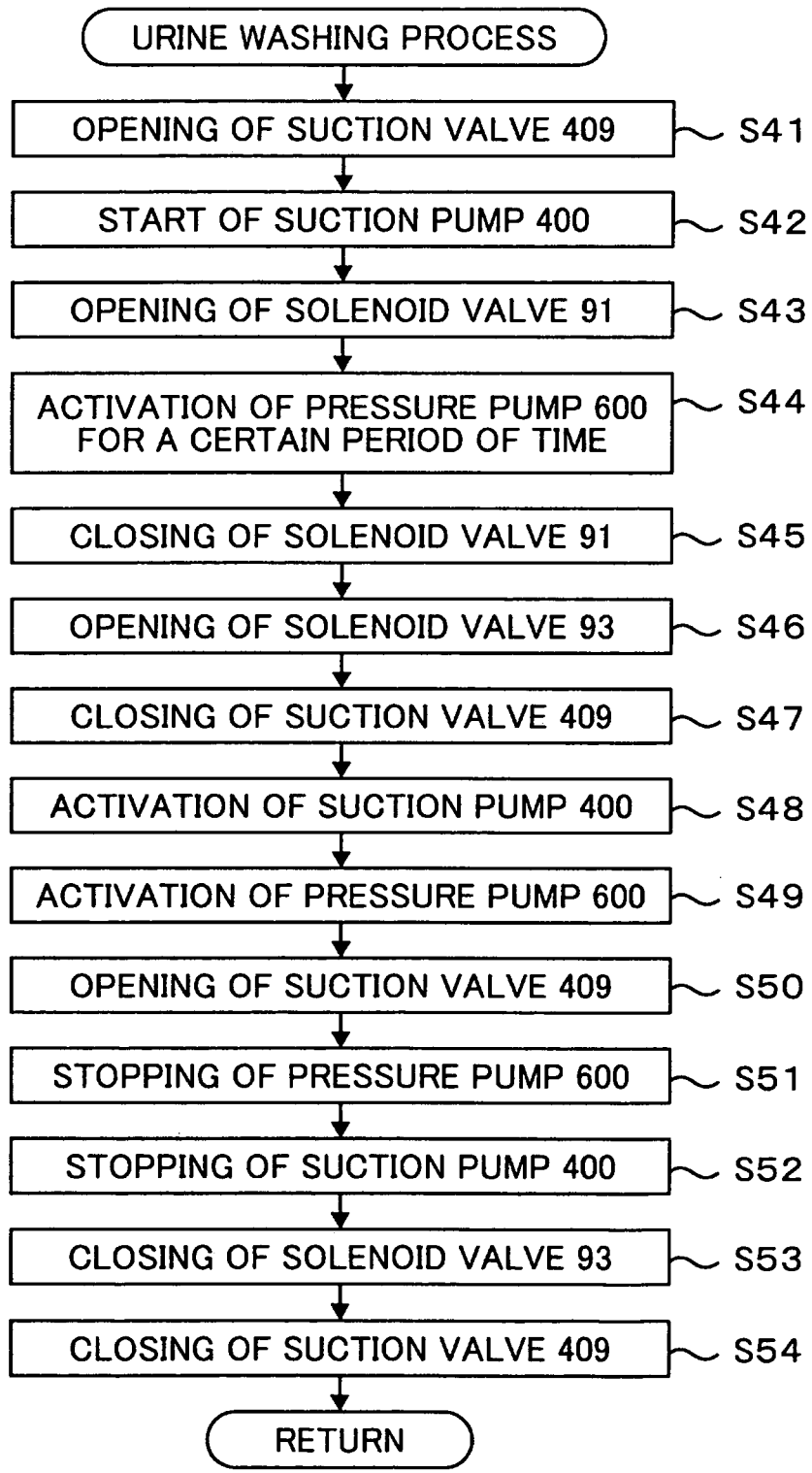
FIG. 17 is a flow chart showing the steps of a procedure of a urine washing process.

(viii-3) FIG. 17 is a flow chart showing the steps of a procedure of the urine washing process.

First, the suction valve 409 is opened (Step S41) and the suction pump 400 is activated (Step S42). Next, after the solenoid valve 91 is opened (Step S43), the pressure pump 600 is activated for a certain period of time (Step S44). With this, the urine is sucked into the storage tank 300 and simultaneously, the buttocks washing operation and the bidet washing operation are executed.

Next, the solenoid valve 91 is closed (Step S35) and then, the solenoid valve 93 is opened (Step S46). Then, after the suction valve 409 is closed (Step S47), the suction pump 400 is activated (Step S48). With this, the vacuum forming operation within the vacuum tank 408 is initiated.

After a predetermined time, the pressure pump 600 is activated and the warm water sent from the hot water tank 501 of the raw water tank 500 is injected as wash water from the injection nozzle 105 through the injection nozzle pipe 604 to push the urine toward the discharge passage 81 (Step S49). At about the same time, the suction valve 409 is opened (Step S50). At this moment, the urine is sucked and housed into the storage tank 300 through the discharge port 102a, the one-way valve casing 66, and the discharge pipe 103 by the maximum vacuum pressure.

Then, the pressure pump 600 is stopped (Step S51) and the suction pump 400 is stopped (Step S52). Next, after the solenoid valve 92 is closed (Step S53), the suction valve 409 is closed (Step S54) to complete the urine washing process.

In the stool washing process and the urine washing process described above, the bad odor released from the waste material sucked and housed into the storage tank 300 through the one-way valve casing 66, the bad odor eliminating filters 407a, 407a, and the silencer 407b is discharged outside the suction pump 400 as little as possible. In the urine washing process, when the wash water is injected from the various nozzles, the water level sensor J always detects whether or not the water level within the urination and defecation container 82 is above a certain level. If the water level is above a certain level, the water level sensor J forcibly stops the injection of wash water from the various nozzles and forcibly causes the waste material within the urination and defecation container 82 to be sucked and housed into the storage tank 300 through the discharge pipe 103.

Figure 18:
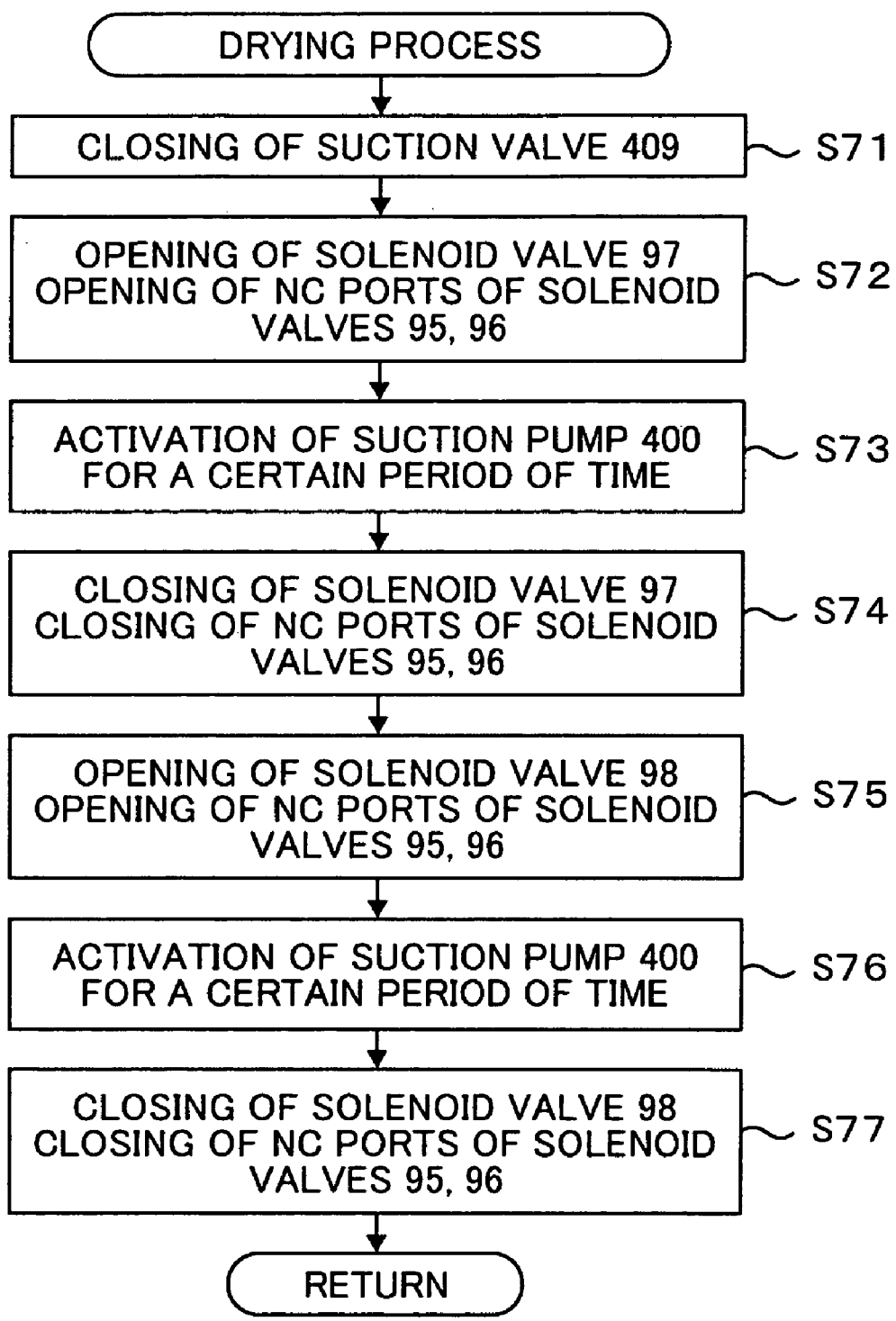
FIG. 18 is a flow chart showing the steps of a procedure of a drying process.

(viii-4) FIG. 18 is a flow chart showing the steps of a procedure of the drying process.

The suction valve 409 is closed (Step S71) and after the solenoid valve 97, and the NC ports of the solenoid valves 95, 96 are opened (Step S72), the suction pump 400 is activated for a certain period of time (Step S73). Air introduced from the silencer 404 is heated at the heater section 63 through the air supply pipe 601b, the solenoid valve 97, and drying nozzle pipe 608 and is sent as dry, warm air from the drying nozzle 204, thereby drying the private parts and buttocks of the human body and the inside of the urination and defecation treating unit 51 with the dry air. After activating the suction pump 400 for a certain period of time, the solenoid valve 97 and the NC ports of the solenoid valves 95, 96 are closed (Step S74).

After opening the solenoid valve 98, and the NC ports of the solenoid valves 95, 96 (Step S75), the suction pump 400 is activated for a certain period of time (Step S76). The air introduced from the silencer 404 is sent as dry air blasting from the air supply nozzle 205 via the air supply pipe 601*b*, the solenoid valve 98, and the air supply nozzle pipe 609, thereby drying the buttocks and the lumbar region of a human body. After activating the suction pump 400 for a certain period of time, the solenoid valve 98 and the NC ports of the solenoid valves 95, 96 are closed (Step S77) to complete the drying process. With this, the air introduced from the silencer 404 is sent as dry air from the drying nozzle 204 and the air supply nozzle 205. Thus, the private parts, buttocks, external lumbar region of the human body and the inside of the urination and defecation treating unit 51 can be dried in a short time.

As shown in FIG. 15, once the washing process (Step S3 or Step S4) and the drying process (Step S7) for the human body and the inside of the urination and defecation treating unit 51 are completed by a series of treatment, the program returns to Step S2 to execute the detection of stools and urine again.

As described above, in the automatic treating device K for urination and defecation according to the present embodiment, the manual defecation treating mode which is carried out when instructed by the patient is available as an operation mode as well as the automatic defecation treating mode. In this manual defecation treating mode, the automatic treating device K for urination and defecation does not carry out sensing (detection) by the stools sensor and the urine sensor, but carries out the defecation treatment only when instructed by the patient to carry out one or the other of the stools washing process and the urine washing process. The patient gives operating instructions using an operation panel provided in place of the automatic treating device K for urination and defecation or a remote-controller. The operation in the manual defecation treating mode will now be described.

Figure 19:
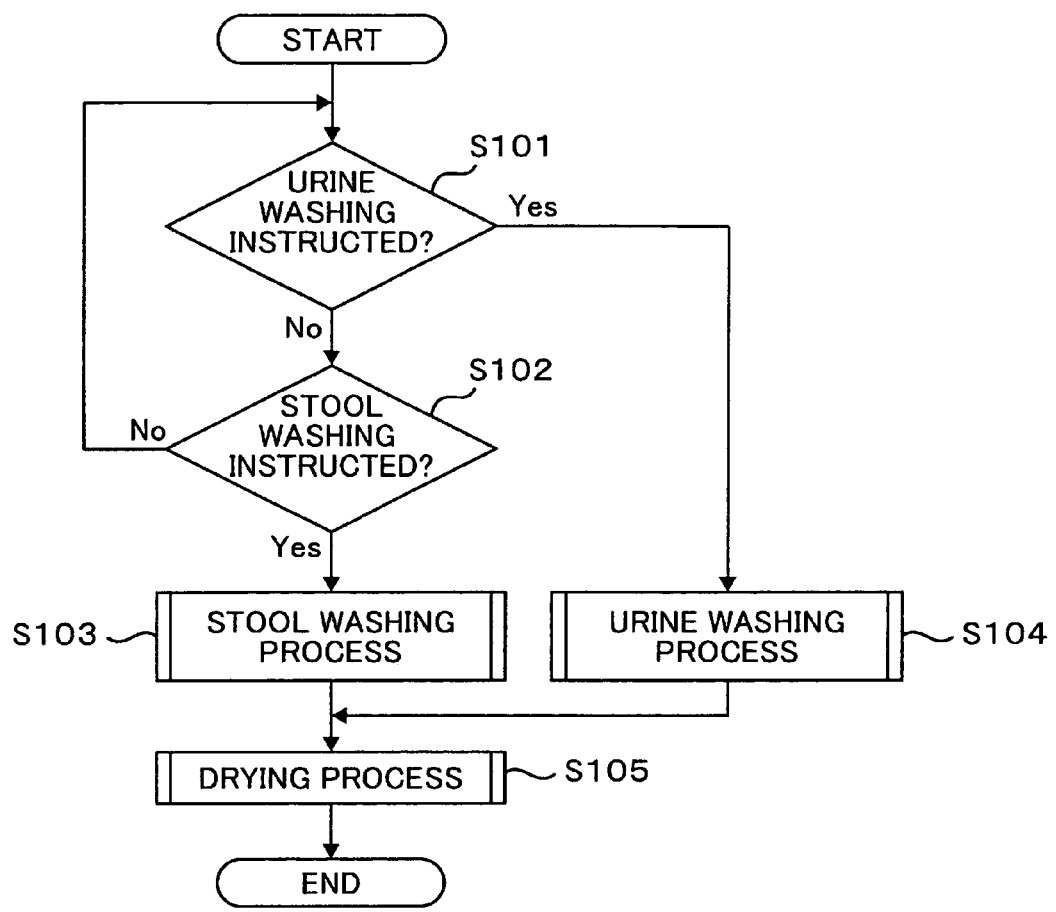
FIG. 19 is a flow chart showing the steps of a procedure of the automatic treating device for urination and defecation in a manual defecation treating mode.

(viii-5) FIG. 19 is a flow chart showing the steps of a procedure of the automatic treating device K for urination and defecation in the manual defecation treating mode.

In the case where the urination washing instructions are given by the patient (Step S101: YES), the urine washing process is carried out in the same procedure as that in the automatic defecation treating mode (Step S104). When the urine washing instructions are not given (Step S101: NO), but the stool washing instructions are given (Step S102: YES), the stool washing process is carried out according to the same procedure as in that in the automatic defecation treating mode described above (Step S103). On the other hand, in the case where neither the urine washing instructions (Step S101: NO) nor the stool washing instructions are given (Step S102: NO), the program waits until instructions are given.

After completing the stool washing process (Step S103) or the urine washing process (Step S104), in order to dry the private parts, buttocks, lumber region of the human body and the inside of the urination and defecation treating unit 51, the drying process is carried out (Step S105) according to the same procedure as the drying process in the automatic defecation treating mode described above to complete the manual defecation treating mode.

EFFECTS OF THE INVENTION

According to the first aspect of the present invention, a toilet unit for use in a supine position is provided in such a manner that a U-shaped casing is fitted into a depressed section of a mattress and a butt-pad is mounted on the U-shaped casing. Next, after a patient is caused to lie supine on the mattress, a substantially T-shaped urination and defecation treating unit is loosely fitted into a U-shaped central groove section of the butt-pad and then, fitted into the crotch of the patient's legs. In this manner, the urination and defecation treating unit is easily detachable. Even in the case where the patient cannot fit the urination and defecation treating unit by his own efforts, the treating unit can be readily applied to the patient with the help of one care provider by following the above procedure. In the case where the urination and defecation treating unit is detached from. the patient, it is possible to readily detach the urination and defecation treating unit because the patient's buttocks protruding from the urination and defecation treating unit contact the butt-pad which bears the weight of the buttocks of the patient. When the urination and defecation treating unit is fitted holding the treating unit in the crotch of the patient's legs, the buttocks of the patient protruding out of the urination and defecation treating unit can be supported by the butt-pad to stabilize the weight around the buttocks and the crotch of the patient's legs can also be fitted into the urination and defecation treating unit, thereby being capable of fitting to the patient.

It is also possible to prevent bedsores from being generated on the buttocks of a bed-ridden patient even though the urination and defecation treating unit is applied to the patient for a long time. In the case where the wash water leaks out of the urination and defecation treating unit, the leaked water is stored in a U-shaped casing under the urination and defecation treating unit and as a result, the reverse side of the bed can be prevented from being directly wetted by the water leakage. The urination and defecation treating unit comprises a lateral casing of which the inside is formed in a boat shape to discharge the urination and defecation to the outside by water supplied from a nozzle provided in the bottom section and a vertical casing having a nozzle provided in front for washing and then drying the buttocks and private parts by air supply. Thus, it is possible to assemble and disassemble the urination and defecation treating unit of a simplified structure in a short time because a frame formed for a diaper to which conventional nozzles are installed is no longer needed and each nozzle can be directly installed on the lateral and vertical casings. A dead end of the lateral casing of the urination and defecation treating unit is communicatively connected to a storage tank through a discharge pipe, while various nozzles provided on both the lateral and vertical casings are communicatively connected to a wash water supply section through a nozzle operating section designed to control the water supply and air supply. Thus, it is possible to automatically carry out the urination and defecation treatment of a patient in a supine position and the washing and drying treatment of the patient's buttocks and private parts while controlling these treatment by the nozzle operating section.

According to the second aspect of the present invention, the U-shaped central groove section of the butt-pad can be integral with the guide passage because the guide wall provided in the middle of the U-shaped casing is fitted into the substantially U-shaped central groove section of the butt-pad.

According to the third aspect of the present invention, the guide passage of the U-shaped casing can be integral with the lateral casing of the urination and defecation treating unit because the lateral casing of the urination and defecation treating unit is loosely fitted into the guide passage formed by the guide wall of the U-shaped casing.

According to the fourth aspect of the present invention, the urination and defecation treating unit of an inverted T-shape is fitted into a support casing of a substantially oblong shape which is fitted into the central groove section of the butt-pad. Thus, in the case where a care provider applies the toilet seat for use in a supine position to a patient who is lying supine, the butt-pad is mounted on the support casing and the care provider places the buttocks of the patient on the butt-pad. In this manner, the urination and defecation treating unit can not only be fitted into the central groove section of the butt-pad, but also can be provided to contact the crotch of the legs and buttocks of the patient. Further, since a treating body is integrally formed in a substantially T-shape by a urination and defecation container of which the inside is formed in a boat shape and a washing nozzle retainer provided upright on the downstream side of the urination and defecation container, the treating body can be used for a long time without causing shape distortion even though the load from the buttocks and crotch of the legs of the patient is applied to the urination and defecation container and the washing nozzle retainer.

It is to be noted that some of the preferred embodiments of the present invention have been described with reference to the drawings, but these are examples and various changes may be made without departing from the spirit and technical scope of the present invention.

What is claimed is:

1. An automatic treating device for urination and defecation having a toilet unit for use in a supine position, the toilet unit comprising:
    a depressed section formed in a substantially rectangular shape in a substantially middle position of a mattress;
    a pipe passage which is communicated with an end of the depressed section and is open to an outside of the mattress;
    a U-shaped casing fitted into the depressed section and adapted to mount a butt-pad provided with a U-shaped central groove section thereon; and
    a urination and defecation treating unit of a substantially T-shape loosely fitted into the U-shaped central groove section of the butt-pad;
    the U-shaped casing being formed in a box shape which corresponds to the substantially rectangular shape of the depressed section and is open upward, an outer shape of the U-shaped casing being formed in a shape loosely fitted into the depressed section, an outer peripheral wall being provided on an outer peripheral edge of a bottom plate of the U-shaped casing, a band-shaped guide passage being provided longitudinally in a center position of the bottom plate, and a guide wall being provided on both sides of the guide passage,
    the guide passage being formed to protrude outside the outer peripheral wall on a downstream side from a distal end of the bottom plate, a distal end of a protruding section of the guide passage is formed to be open, and when mounting the U-shaped casing on the depressed section of the mattress, the protruding section of the guide passage being inserted into the pipe passage communicated with the depressed section of the mattress,
    the urination and defecation treating unit being formed in an inverted T-shape by a lateral casing, of which the inside is formed in a boat shape to discharge urination and defecation externally by water discharged from a nozzle provided on a bottom section of the urination and defecation treating unit, and a vertical casing with a nozzle provided in front for washing the buttocks and private parts of a human body and then drying the buttocks and private parts by an air supply;
    wherein a distal end of the lateral casing of the urination and defecation treating unit is communicatively connected to a storage tank through a discharge pipe, various nozzles provided on the lateral and vertical casings are communicatively connected to a wash water supply section through a nozzle operating section designed to control water and air supply, and the lateral casing of the urination and defecation treating unit is loosely fitted into the guide passage of the U-shaped casing when fitting the urination and defecation treating unit into a U-shaped central groove position of the butt-pad.

\* \* \* \* \*